US010626460B2

(12) United States Patent
Morrow et al.

(10) Patent No.: US 10,626,460 B2
(45) Date of Patent: Apr. 21, 2020

(54) USE OF GLYCANS AND GLYCOSYLTRANSFERASES FOR DIAGNOSING/MONITORING INFLAMMATORY BOWEL DISEASE

(71) Applicant: Children's Hospital Medical Center, Cincinnati, OH (US)

(72) Inventors: Ardythe L. Morrow, Cincinnati, OH (US); Lee A. Denson, Wyoming, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 692 days.

(21) Appl. No.: 14/767,116

(22) PCT Filed: Feb. 21, 2014

(86) PCT No.: PCT/US2014/017630
§ 371 (c)(1),
(2) Date: Dec. 24, 2015

(87) PCT Pub. No.: WO2014/130789
PCT Pub. Date: Aug. 28, 2014

(65) Prior Publication Data
US 2015/0376696 A1 Dec. 31, 2015

Related U.S. Application Data

(60) Provisional application No. 61/767,500, filed on Feb. 21, 2013.

(51) Int. Cl.
| C12Q 1/68 | (2018.01) |
| C12Q 1/6876 | (2018.01) |
| C12Q 1/48 | (2006.01) |
| G01N 33/80 | (2006.01) |
| C12Q 1/6883 | (2018.01) |
| G01N 33/53 | (2006.01) |

(52) U.S. Cl.
CPC ............ *C12Q 1/6876* (2013.01); *C12Q 1/48* (2013.01); *C12Q 1/6883* (2013.01); *G01N 33/5308* (2013.01); *G01N 33/80* (2013.01); *C12Q 2600/112* (2013.01); *C12Q 2600/158* (2013.01); *G01N 2333/91091* (2013.01); *G01N 2800/065* (2013.01); *G01N 2800/52* (2013.01); *G01N 2800/56* (2013.01)

(58) Field of Classification Search
None
See application file for complete search history.

(56) References Cited

U.S. PATENT DOCUMENTS

| 3,681,373 A | 8/1972 | Adams et al. |
| 5,470,843 A | 11/1995 | Stahl et al. |
| 5,474,986 A | 12/1995 | Magnusson et al. |
| 5,484,773 A | 1/1996 | Heerze et al. |
| 5,576,300 A | 11/1996 | Mukerji et al. |
| 5,635,606 A | 6/1997 | Heerze et al. |
| 5,700,671 A | 12/1997 | Prieto et al. |
| 5,892,070 A | 4/1999 | Prieto et al. |
| 5,919,913 A | 7/1999 | Nuyens et al. |
| 6,045,854 A | 4/2000 | Prieto et al. |
| 6,126,961 A | 10/2000 | Kross |
| 6,132,710 A | 10/2000 | Panigrahi et al. |
| 6,146,670 A | 11/2000 | Prieto et al. |
| 6,204,431 B1 | 3/2001 | Prieto et al. |
| 6,291,435 B1 | 9/2001 | Yanmaele et al. |
| 6,540,999 B1 | 4/2003 | Harn et al. |
| 7,871,785 B2 | 1/2011 | Morrow et al. |
| 7,893,041 B2 | 2/2011 | Morrow et al. |
| 8,314,061 B2 | 11/2012 | Morrow et al. |
| 8,574,850 B2 | 11/2013 | Morrow et al. |
| 9,034,847 B2 | 5/2015 | Morrow et al. |
| 9,132,142 B2 | 9/2015 | Morrow et al. |
| 9,132,143 B2 | 9/2015 | Morrow et al. |
| 2002/0019991 A1 | 2/2002 | Prieto et al. |
| 2002/0058313 A1 | 5/2002 | Renkonen et al. |
| 2002/0115839 A1 | 8/2002 | Meyers et al. |
| 2003/0036070 A1 | 2/2003 | Chakravarti |
| 2004/0131659 A1 | 7/2004 | Gibson |
| 2006/0040893 A1 | 2/2006 | Harn et al. |
| 2007/0020660 A1 | 1/2007 | Burczynski et al. |
| 2007/0134251 A1 | 6/2007 | Ashkenazi et al. |
| 2007/0275881 A1 | 11/2007 | Morrow et al. |
| 2009/0098240 A1 | 4/2009 | Mills et al. |
| 2009/0169535 A1 | 7/2009 | Marth |
| 2011/0177035 A1 | 7/2011 | Morrow et al. |
| 2011/0207659 A1 | 8/2011 | Morrow et al. |
| 2012/0202753 A1 | 8/2012 | Morrow et al. |
| 2012/0294840 A1 | 11/2012 | Newburg et al. |
| 2014/0140970 A1 | 5/2014 | Morrow et al. |
| 2015/0079055 A1 | 3/2015 | Morrow et al. |
| 2015/0306120 A1 | 10/2015 | Morrow et al. |
| 2018/0153915 A1 | 6/2018 | Morrow et al. |

FOREIGN PATENT DOCUMENTS

| EP | 451462 A1 | 10/1991 |
| EP | 0 870 841 A1 | 10/1998 |
| EP | 1 199 364 A2 | 4/2002 |
| EP | 2 631 650 A1 | 8/2013 |
| JP | 2002-218996 A | 8/2002 |

(Continued)

OTHER PUBLICATIONS

PCT/US2014/017630, Jul. 21, 2014, International Search Report and Written Opinion.

(Continued)

*Primary Examiner* — Jehanne S Sitton
(74) *Attorney, Agent, or Firm* — Polsinelli PC; Yahua Chen

(57) ABSTRACT

Diagnostic methods for assessing risk of or presence of inflammatory bowel disease in a patient based on glycosyltransferase or histo-blood group antigen signatures or a combination thereof. Also disclosed herein are prognostic methods for monitoring inflammatory bowel disease progression in a patient.

8 Claims, 16 Drawing Sheets

(56) References Cited

FOREIGN PATENT DOCUMENTS

| JP | 2004-528529 A | 9/2004 |
|---|---|---|
| JP | 2006-506329 A | 2/2006 |
| JP | 2009-532372 A | 9/2009 |
| WO | WO 92/18610 A2 | 10/1992 |
| WO | WO 94/18986 A1 | 9/1994 |
| WO | WO 95/24495 A1 | 9/1995 |
| WO | WO 99/31224 A2 | 6/1999 |
| WO | WO 99/056754 | 11/1999 |
| WO | WO 2002/043578 A2 | 6/2002 |
| WO | WO 2004/041291 A1 | 5/2004 |
| WO | WO 2005/039319 A2 | 5/2005 |
| WO | WO 2005/055944 A2 | 6/2005 |
| WO | WO 2005/110121 A1 | 11/2005 |
| WO | WO 2006/017859 A2 | 2/2006 |
| WO | WO 2006/091103 A2 | 8/2006 |
| WO | WO 2006/133533 A1 | 12/2006 |
| WO | WO 2007/087468 A2 | 8/2007 |
| WO | WO 2007/090894 A1 | 8/2007 |
| WO | WO 2009/033011 A1 | 3/2009 |
| WO | WO 2009/077352 A1 | 6/2009 |
| WO | WO 2011/005681 A1 | 1/2011 |
| WO | WO 2013/025104 A1 | 2/2013 |

OTHER PUBLICATIONS

PCT/US2014/017630, Sep. 3, 2015, International Preliminary Report on Patentability.
PCT/US2014/017630, May 14, 2014, Invitation to Pay Additional Fees.
Beck et al., Exploring the interplay of barrier function and leukocyte recruitment in intestinal inflammation by targeting fucosyltransferase VII and trefoil factor 3. Am J Physiol Gastrointest Liver Physiol. Jul. 2010;299(1):G43-53. doi: 10.1152/ajpgi.00228.2009. Epub Mar. 18, 2010.
Brazil et al., α3/4 Fucosyltransferase 3-Dependent Synthesis of Sialyl Lewis A on CD44 Variant Containing Exon 6 Mediates Polymorphonuclear Leukocyte Detachment from Intestinal Epithelium during Transepithelial Migration. J Immunol. Nov. 1, 2013;191(9):4804-17. doi: 10.4049/jimmunol.1301307. Epub Sep. 25, 2013.
Chaturvedi et al., Fucosylated human milk oligosaccharides vary between individuals and over the course of lactation. Glycobiology. May 2001;11(5):365-72.
Conway et al., p40phox expression regulates neutrophil recruitment and function during the resolution phase of intestinal inflammation. J Immunol. Oct. 1, 2012;189(7):3631-40. Epub Aug. 22, 2012.
Dooley et al., Regulation of gene expression in inflammatory bowel disease and correlation with IBD drugs: screening by DNA microarrays. Inflamm Bowel Dis. Jan. 2004;10(1):1-14.
Henry, Molecular diversity in the biosynthesis of GI tract glycoconjugates. A blood-group-related chart of microorganism receptors. Transfus Clin Biol. Jun. 2001;8(3):226-30. Review.
Huang et al., Noroviruses bind to human ABO, Lewis, and secretor histo-blood group antigens: identification of 4 distinct strain-specific patterns. J Infect Dis. Jul. 1, 2003;188(1):19-31. Epub Jun. 12, 2003.
Loftus., Clinical epidemiology of inflammatory bowel disease: Incidence, prevalence, and environmental influences. Gastroenterology. May 2004;126(6):1504-17.
McGovern et al., Fucosyltransferase 2 (FUT2) non-secretor status is associated with Crohn's disease. Hum Mol Genet. Sep. 1, 2010;19(17):3468-76. doi: 10.1093/hmg/ddq248. Epub Jun. 22, 2010.
Morrow et al., Fucosyltransferase 2 non-secretor and low secretor status predicts severe outcomes in premature infants. J Pediatr. May 2011;158(5):745-51. doi: 10.1016/j.jpeds.2010.10.043. Epub Jan. 22, 2011.
Nakayama et al., CD15 Expression in Mature Granulocytes Is Determined by α1,3-Fucosyltransferase IX, but in Promyelocytes and Monocytes by α1,3-Fucosyltransferase IV. J Biol Chem. May 11, 2001;276(19):16100-6. doi: 10.1074/jbc.M007272200. Epub Feb. 23, 2001.
Park et al., Inflammatory bowel disease—attributable costs and cost-effective strategies in the United States: a review. Inflamm Bowel Dis. Jul. 2011;17(7):1603-9. doi: 10.1002/ibd.21488. Epub Nov. 4, 2010. Review.
Rausch et al., Colonic mucosa-associated microbiota is influenced by an interaction of Crohn disease and FUT2 (Secretor) genotype. Proc Natl Acad Sci U S A. Nov. 22, 2011;108(47):19030-5. doi: 10.1073/pnas.1106408108. Epub Nov. 8, 2011.
Thurl et al., Detection of four human milk groups with respect to Lewis blood group dependent oligosaccharides. Glycoconj J. Nov. 1997;14(7):795-9.
Viverge et al., Discriminant carbohydrate components of human milk according to donor secretor types. J Pediatr Gastroenterol Nutr. Oct. 1990;11(3):365-70.
[No Author Listed], definition for term "entero-"; The Free Dictionary. http://www.thefreedictionary.com/entero-. Retrieved Jan. 13, 2016. 1 page.
[No Author Listed], definition for term "-itis"; The Free Dictionary. http://www.thefreedictionary.com/-itis. Retrieved Jan. 13, 2016. 1 page.
[No Author Listed], Dorland's Illustrated Medical Dictionary, 27th Edition, 1988, p. 228.
[No Author Listed], Quantikine Total Adiponectin ELISA Kit. Retrieved from http://www.funakoshi.co.jp/contents/6797. Last accessed Dec. 18, 2014.
Albermann et al., Synthesis of the milk oligosaccharide 2'-fucosyllactose using recombinant bacterial enzymes. Carbohydr Res. Aug. 23, 2001;334(2):97-103.
Anderson et al., Improved method for the isolation of 2' fucosyllactose from human milk. J.Chromatogr. Jun. 26, 1981;211(1):170-4.
Barclay et al., Systematic review: the role of breastfeeding in the development of pediatric inflammatory bowel disease. J Pediatr. Sep. 2009;155(3):421-6. doi:10.1016/j.jpeds.2009.03.017. Epub May 22, 2009.
Bin-Nun et al., Oral probiotics prevent necrotizing enterocolitis in very low birth weight neonates. J Pediatr. Aug. 2005;147(2):192-6.
Blackwell, The role of ABO blood groups and secretor status in host defences. FEMS Microbiol Immunol. Jun. 1989;1(6-7):341-9.
Bode et al., Human milk oligosaccharides reduce platelet-neutrophil complex formation leading to a decrease in neutrophil beta 2 integrin expression. J Leukoc Biol. Oct. 2004;76(4):820-6. Epub Jul. 7, 2004.
Bode et al., Inhibition of monocyte, lymphocyte, and neutrophil adhesion to endothelial cells by human milk oligosaccharides. Thromb Haemost. Dec. 2004;92(6):1402-10.
Bode, Recent advances on structure, metabolism, and function of human milk oligosaccharides. J Nutr. Aug. 2006;136(8):2127-30. Review.
Boehm et al., Oligosaccharides from milk. J Nutr. Mar. 2007;137(3 Suppl 2):847S-9S.
Boehm et al., Supplementation of a bovine milk formula with an oligosaccharide mixture increases counts of faecal bifidobacteria in preterm infants. Arch Dis Child Fetal Neonatal Ed. May 2002;86(3):F178-81.
Brown et al., Altered immune system glycosylation causes colitis in alpha1,2-fucosyltransferase transgenic mice. Inflamm Bowel Dis. Sep. 2004;10(5):546-56.
Buescher. Anti-inflammatory characteristics of human milk: how, where, why. Adv Exp Med Biol. 2001;501:207-22.
Caplan et al., Bifidobacterial supplementation reduces the incidence of necrotizing enterocolitis in a neonatal rat model. Gastroenterology. Sep. 1999;117(3):577-83.
Catala et al., Oligofructose contributes to the protective role of bifidobacteria in experimental necrotising enterocolitis in quails. J Med Microbiol. Jan. 1999;48(1):89-94.

(56) References Cited

OTHER PUBLICATIONS

Chaturvedi et al., Milk oligosaccharide profiles by reversed-phase HPLC of their perbenzoylated derivatives. Anal Biochem. Aug. 15, 1997;251(1):89-97.
Chen et al., Probiotics and prebiotics: role in clinical disease states. Adv Pediatr. 2005;52:77-113.
Cheromcha et al., Neonatal necrotizing enterocolitis. Inflammatory bowel disease of the newborn. Dig Dis Sci. Mar. 1988;33(3 Suppl):78S-84S. Abstract.
Chirico et al., Antiinfective properties of human milk. J Nutr. Sep. 2008;138(9):1801S-1806S.
Claud, Neonatal Necrotizing Enterocolitis—Inflammation and Intestinal Immaturity. Antiinflamm Antiallergy Agents Med Chem. Sep. 2009;8(3):248-259. Abstract.
Collins et al., Probiotics, prebiotics, and synbiotics: approaches for modulating the microbial ecology of the gut. Am J Clin Nutr. May 1999;69(5):1052S-1057S. Review.
Cooper et al., Immunohistologic study of ulcerative colitis with monoclonal antibodies against tumor-associated and/or differentiation antigens. Gastroenterology. Sep. 1988;95(3):686-93.
Coppa et al., Human milk oligosaccharides inhibit the adhesion to Caco-2 cells of diarrheal pathogens: *Escherichia coli*, Vibrio cholerae, and *Salmonella fyris*. Pediatr Res. Mar. 2006;59(3):377-82.
Cordon-Cardo et al., Immunohistologic expression of blood-group antigens in normal human gastrointestinal tract and colonic carcinoma. Int J Cancer. May 15, 1986;37(5):667-76.
Cregg et al., Recombinant protein expression in Pichia pastoris. Mol Biotechnol. Sep. 2000;16(1):23-52.
D'Adamo et al., Metabolic and immunologic consequences of ABH secretor and Lewis subtype status. Altern Med Rev. Aug. 2001;6(4):390-405.
Daddaoua et al., Goat milk oligosaccharides are anti-inflammatory in rats with hapten-induced colitis. J Nutr. Mar. 2006;136(3):672-6.
Dai et al., Role of oligosaccharides and glycoconjugates in intestinal host defense. J Pediatr Gastroenterol Nutr. 2000;30 Suppl 2:S23-33.
Dean et al., The VRG4 gene is required for GDP-mannose transport into the lumen of the Golgi in the yeast, *Saccharomyces cerevisiae*. J Biol Chem. Dec. 12, 1997;272(50):31908-14.
Eiwegger et al., Human milk-derived oligosaccharides and plant-derived oligosaccharides stimulate cystokine production of cord blood T-cells in vitro. Pediatr Res. Oct. 2004;56(4):536-40. Epub Aug. 4, 2004.
Ewaschuk et al., Probiotics and prebiotics in chronic inflammatory bowel diseases. World J Gastroenterol. Oct. 7, 2006;12(37):5941-50. Review.
Frost et al., The importance of pro-inflammatory signaling in neonatal necrotizing enterocolitis. Semin Perinatol. Apr. 2008;32(2):100-6. doi: 10.1053/j.semperi.2008.01.001.
Gao et al., Identification of a conserved motif in the yeast golgi GDP-mannose transporter required for binding to nucleotide sugar. J Biol Chem. Feb. 9, 2001;276(6):4424-32. Epub Nov. 6, 2000.
Gokmen-Polar et al., Elevated protein kinase C betaII is an early promotive event in colon carcinogenesis. Cancer Res. Feb. 15, 2001;61(4):1375-81.
Grazioso et al., Anti-inflammatory effect of human milk feeding on chemically induced colitis in rats. Pediatric Research. 1996;39;119. Abstract.
Grazioso et al., Anti-inflammatory effects of human milk on chemically induced colitis in rats. Pediatr Res. Nov. 1997;42(5):639-43.
Hällström et al., Effects of mode of delivery and necrotising enterocolitis on the intestinal microflora in preterm infants. Eur J Clin Microbiol Infect Dis. Jun. 2004;23(6):463-70. Epub May 27, 2004.
Hanisch et al., Structures of acidic O-linked polylactosaminoglycans on human skim milk mucins. Glycoconj J. 1990;7(6):525-43.
Hanisch et al., Structures of neutral O-linked polylactosaminoglycans on human skim milk mucins. A novel type of linearly extended poly-N-acetyllactosamine backbones with Gal beta(1-4)GlcNAc beta(1-6) repeating units. J Biol Chem. Jan. 15, 1989;264(2):872-83.

Haynes et al., Proteome analysis: biological assay or data archive? Electrophoresis. Aug. 1998;19(11):1862-71.
Heneghan et al., Effect of host Lewis and ABO blood group antigen expression on Helicobacter pylori colonisation density and the consequent inflammatory response. FEMS Immunol Med Microbiol. Apr. 1998;20(4):257-66.
Hurd et al., Increased susceptibility of secretor factor gene Fut2-null mice to experimental vaginal candidiasis. Infect Immun Jul. 2004;72(7):4279-81.
Ikehara et al., Polymorphisms of two fucosyltransferase genes (Lewis and Secretor genes) involving type I Lewis antigens are associated with the presence of anti-Helicobacter pylori IgG antibody. Cancer Epidemiol Biomarkers Prev. Sep. 2001;10(9):971-7.
Imaoka et al., Anti-inflammatory activity of probiotic Bifidobacterium: enhancement of IL-10 production in peripheral blood mononuclear cells from ulcerative colitis patients and inhibition of IL-8 secretion in HT-29 cells. World J Gastroenterol. Apr. 28, 2008;14(16):2511-6.
Jiang et al., Prevalence of enteric pathogens among international travelers with diarrhea acquired in Kenya (Mombasa), India (Goa), or Jamaica (Montego Bay). J Infect Dis. Feb. 15, 2002;185(4):497-502. Epub Jan. 22, 2002.
Jones et al., Induction of proinflammatory responses in the human monocytic cell line THP-1 by Campylobacter jejuni. Infect Immun. May 2003;71(5):2626-33.
Kafetzis et al., Neonatal necrotizing enterocolitis: an overview. Curr Opin Infect Dis. Aug. 2003;16(4):349-55.
Kim et al., Expression of LeY and extended LeY blood group-related antigens in human malignant, premalignant, and nonmalignant colonic tissues. Cancer Res. Nov. 1986;46(11):5985-92.
Klement et al., Breastfeeding and risk of inflammatory bowel disease: a systematic review with meta-analysis. Am J Clin Nutr. Nov. 2004;80(5):1342-52.
Kobayashi et al., Lewis blood group-related antigen expression in normal gastric epithelium, intestinal metaplasia, gastric adenoma, and gastric carcinoma. Am J Gastroenterol. Jun. 1993;88(6):919-24.
Konopka et al., Variable expression of the translocated c-abl oncogene in Philadelphia chromosome-positive B-lymphoid cell lines from chronic myelogenous leukemia patients. Proc Natl Acad Sci U S A. Jun. 1986;83(11):4049-52.
Kunz et al., Oligosaccharides in human milk: structural, functional, and metabolic aspects. Annu Rev Nutr. 2000;20:699-722.
Kunz et al., Potential Anti-Inflammatory and Anti-Infectious Effects of Human Milk Oligosaccharides, Bioactive Components of Milk (Book Series: Advances in Experimental Medicine and Biology, Springer Science & Business Media, New York, NY, US, XP009136897, ISBN: 978-0-387-74086-7: 455-465. 2008.
Lara-Villoslada et al., Oligosaccharides isolated from goat milk reduce intestinal inflammation in a rat model of dextran sodium sulfate-induced colitis. Clin Nutr. Jun. 2006;25(3):477-88. Epub Jan. 10, 2006.
Le Pendu, Histo-blood group antigen and human milk oligosaccharides: genetic polymorphism and risk of infectious diseases. Adv Exp Med Biol. 2004;554:135-43.
Leiper et al., Altered Expression of Fucosyl-Transferases in Inflammatory Bowel Disease. Gastroenterology. 2001;120:A-525, Abstract #2671.
Lewin. Genes VI. Chapter 29—Regulation of transcription. Oxford University Press. 1997: 847-48.
Lin et al., Oral probiotics reduce the incidence and severity of necrotizing enterocolitis in very low birth weight infants. Pediatrics. Jan. 2005;115(1):1-4.
Lucas et al., Breast milk and neonatal necrotising enterocolitis. Lancet. Dec. 22-29, 1990;336(8730):1519-23.
Madjd et al., High expression of Lewis y/b antigens is associated with decreased survival in lymph node negative breast carcinomas. Breast Cancer Res. 2005;7(5):R780-7. Epub Jul. 28, 2005.
Maki, Conversion of GDP-Mannose into Various GDP-Deoxyhexoses in Gram-Negative Bacteria. Academic Dissertation. University of Helsinki, Jun. 16, 2003: 1-63.
Mattila et al., Functional expression of *Escherichia coli* enzymes synthesizing GDP-L-fucose from inherent GDP-D-mannose in *Saccharomyces cerevisiae*. Glycobiology. Oct. 2000;10(10):1041-7.

(56) References Cited

OTHER PUBLICATIONS

Meyrand et al., Comparison of milk oligosaccharides between goats with and without the genetic ability to synthesize α(s1)-casein. Small Rumin Res. Jul. 1, 2013;113(2-3):411-420.

Mikhailov et al., Breastfeeding and genetic factors in the etiology of inflammatory bowel disease in children. World J Gastroenterol. Jan. 21, 2009;15(3):270-9.

Morland et al., Promotion of leukocyte transendothelial cell migration by chemokines derived from human biliary epithelial cells in vitro. Proc Assoc Am Physicians. Jul. 1997;109(4):372-82.

Morrow et al., Human milk oligosaccharide blood group epitopes and innate immune protection against campylobacter and calicivirus diarrhea in breastfed infants. Adv Exp Med Biol. 2004;554:443-6.

Morrow et al., Human milk oligosaccharides are associated with protection against diarrhea in breast-fed infants. J Pediatr. Sep. 2004;145(3):297-303.

Morrow et al., Human-milk glycans that inhibit pathogen binding protect breast-feeding infants against infectious diarrhea. J Nutr. May 2005;135(5):1304-7.

Moss et al., Th1/Th2 cells in inflammatory disease states: therapeutic implications. Expert Opin Biol Ther. Dec. 2004;4(12):1887-96.

Nakamura et al., the milk oligosaccharides of domestic farm animals. Trends in glycolscience glycotechnol. Mar. 2004;16(88):135-142.

Nanthakumar et al., Inflammation in the developing human intestine: A possible pathophysiologic contribution to necrotizing enterocolitis. Proc Natl Acad Sci U S A. May 23, 2000;97(11):6043-8.

Newburg et al., Human milk alpha1,2-linked fucosylated oligosaccharides decrease risk of diarrhea due to stable toxin of *E. coli* in breastfed infants. Adv Exp Med Biol. 2004;554:457-61.

Newburg et al., Human milk glycans protect infants against enteric pathogens. Annu Rev Nutr. 2005;25:37-58.

Newburg et al., Innate protection conferred by fucosylated oligosaccharides of human milk against diarrhea in breastfed infants. Glycobiology. Mar. 2004;14(3):253-63. Epub Nov. 24, 2003. Erratum in: Glycobiology. May 2004;14(5):13G.

Newburg et al., Protection of the neonate by the innate immune system of developing gut and of human milk. Pediatr Res. Jan. 2007;61(1):2-8. Review.

Newburg et al., α1,2-linked fucosyloligosaccharides comprise a major component of the innate immune system of human milk. Glycobiology 2003, #233; 13(11):885.

Newburg, Human Milk Glycoconjugates that Inhibit Pathogens. Current Medicinal Chemistry, Bentham Science Publishers BV, BE, vol. 6, No. 2, Jan. 1, 1999: 117-127.

Newburg, Human milk oligosaccharides and glycoconjugates protect the newborn against infection. Pediatric Research. 1999; 45:742. doi:10.1203/00006450-199905010-00027.

Newburg, Neonatal protection by an innate immune system of human milk consisting of oligosaccharides and glycans. J Anim Sci. Apr. 2009;87(13 Suppl):26-34. doi: 10.2527/jas.2008-1347. Epub Nov. 21, 2008.

Notice of Opposition to a European patent 2451462. N.V. Nutricia. Jun. 5, 2018. Brief.

Notice of Opposition to EP 2451462 dated Jun. 5, 2018. N.V. Nutricia.

Notice of Opposition to EP 2451462 dated Jun. 6, 2018. Grunecker.

Notice of Opposition to EP 2451462 dated Jun. 6, 2018. Grunecker. Brief.

Orlando, The immunologic significance of breast milk. J Obstet Gynecol Neonatal Nurs. Sep. 1995;24(7):678-83.

Parashar et al., Diarrheal mortality in US infants. Influence of birth weight on risk factors for death. Arch Pediatr Adolesc Med. Jan. 1998;152(1):47-51.

Pennica et al., WISP genes are members of the connective tissue growth factor family that are up-regulated in wnt-1-transformed cells and aberrantly expressed in human colon tumors. Proc Natl Acad Sci U S A. Dec. 8, 1998;95(25):14717-22.

Podolsky et al., Development of anti-human colonic mucin monoclonal antibodies. Characterization of multiple colonic mucin species. J Clin Invest. Apr. 1986;77(4):1251-62.

Pradel et al., Prevalence and characterization of Shiga toxin-producing *Escherichia coli* isolated from cattle, food, and children during a one-year prospective study in France. J Clin Microbiol. Mar. 2000;38(3):1023-31.

Prestwich et al., Controlled chemical modification of hyaluronic acid: synthesis, applications, and biodegradation of hydrazide derivatives. J Control Release. Apr. 30, 1998;53(1-3):93-103.

Prieto, In vitro and clinical experiences with a human milk oligosaccharide. FFI Journal. 2005;210(11):1018-1029.

Reinhard et al., Image analysis method to assess adhesion of Helicobacter pylori to gastric epithelium using confocal laser scanning microscopy. J Microbiol Methods. Feb. 2000;39(3):179-87.

Rivero et al., Effect of a new infant formula enriched with prebiotics, probiotics, nucleotides and LC-PUFA on recovery after infection. Advances in Experimental Medicine and Biology. 2005;569:186-7.

Rubaltelli et al., Feeding and Neonatal Necrotizing Enterocolitis. In: Nutrition of the Very Low Birthweight Infant. Eds: Ziegler et al. 1999. 199-210.

Rudloff et al., Detection of ligands for selectins in the oligosaccharide fraction of human milk. Eur J Nutr. Apr. 2002;41(2):85-92.

Ruiz-Palacios et al., Campylobacter jejuni binds intestinal H(O) antigen (Fuc alpha 1, 2Gal beta 1, 4GlcNAc), and fucosyloligosaccharides of human milk inhibit its binding and infection. J Biol Chem. Apr. 18, 2003;278(16):14112-20. Epub Jan. 31, 2003.

Saiman et al., Risk factors for candidemia in Neonatal Intensive Care Unit patients. The National Epidemiology of Mycosis Survey study group. Pediatr Infect Dis J. Apr. 2000;19(4):319-24.

Sharon et al., Safe as mother's milk: carbohydrates as future anti-adhesion drugs for bacterial diseases. Glycoconj J. Jul.-Sep. 2000;17(7-9):659-64.

Sisk et al., Early human milk feeding is associated with a lower risk of necrotizing enterocolitis in very low birth weight infants. J Perinatol. Jul. 2007;27(7):428-33. Epub Apr. 19, 2007. Erratum in: J Perinatol. Dec. 2007;27(12):808.

Snelling, Effects of probiotics on the gastrointestinal tract. Curr Opin Infect Dis. Oct. 2005;18(5):420-6.

Spik et al., Primary and three-dimensional structure of lactotransferrin (lactoferrin) glycans. pp. 21-32 from Lactoferrin: Structure and Function, T.W. Hutchens, ed. Plenum Press, New York, 1994.

Spik et al., Primary structure of the glycans from human lactotransferrin. Eur J Biochem. Jan. 1982;121(2):413-9.

Stromqvist et al., Human milk kappa-casein and inhibition of Helicobacter pylori adhesion to human gastric mucosa. J Pediatr Gastroenterol Nutr. Oct. 1995;21(3):288-96.

Thomsson et al., MUC5B glycosylation in human saliva reflects blood group and secretor status. Glycobiology. Aug. 2005;15(8):791-804. Epub Apr. 6, 2005.

Thurl et al., Quantification of individual oligosaccharide compounds from human milk using high-pH anion-exchange chromatography. Anal Biochem. Mar. 15, 1996;235(2):202-6.

Treszl et al., Genetic basis for necrotizing enterocolitis—risk factors and their relations to genetic polymorphisms. Front Biosci. Jan. 1, 2006;11:570-80.

Tsuboi et al., Alpha1,2fucosylation is a superior predictor of postoperative prognosis for colorectal cancer compared with blood group A, B, or sialyl Lewis X antigen generated within colorectal tumor tissues. Ann Surg Oncol. Jun. 2007;14(6):1880-9. Epub Mar. 21, 2007.

Updegrove, Necrotizing enterocolitis: the evidence for use of human milk in prevention and treatment. J Hum Lact. Aug. 2004;20(3):335-9.

Urashima et al., Oligosaccharides of milk and colostrum in non-human mammals. Glycoconj J. May 2001;18(5):357-71.

Urashima et al., Recent advances in studies on milk oligosaccharides of cows and other domestic farm animals. Biosci Biotechnol Biochem. 2013;77(3):455-66. Epub Mar. 7, 2013.

(56) References Cited

OTHER PUBLICATIONS

Urashima et al., Studies of the neutral trisaccharides of goat (*Capra hircus*) colostrum and of the one- and two-dimensional 1H and 13C NMR spectra of 6'-N-acetylglucosaminyllactose. Carbohydr Res. Sep. 15, 1994;262(2):173-84.

Velupillai et al., Oligosaccharide-specific induction of interleukin 10 production by B220+ cells from schistosome-infected mice: a mechanism for regulation of CD4+ T-cell subsets. Proc Natl Acad Sci U S A. Jan. 4, 1994;91(1):18-22.

Wakabayashi et al., Lactoferrin research, technology and applications. Int. Dairy J. 2006; 16:1241-51.

Ward, Isolation of Milk Oligosaccharides using solid-phase extraction. Open Glycoscience. 2009;2:9-15.

Wilson et al., Glycoproteomics of milk: differences in sugar epitopes on human and bovine milk fat globule membranes. J Proteome Res. Sep. 2008;7(9):3687-96. doi:10.1021/pr700793k. Epub Jul. 15, 2008.

Wu et al., Identification and characterization of GDP-d-mannose 4,6-dehydratase and GDP-1-fucose snthetase in a GDP-1-fucose biosynthetic gene cluster from Helicobacter pylori. Biochem Biophys Res Commun. Jul. 13, 2001;285(2):364-71.

Yolken et al., Human milk mucin inhibits rotavirus replication and prevents experimental gastroenteritis. J Clin Invest. Nov. 1992;90(5):1984-91.

Ziemer et al., An Overview of Probiotics, Prebiotics and Synbiotics in the Functional Food Concept: Perspectives and Future Strategies International Dairy Journal. 1998; 8:473-79.

1=Healthy adults, 2=healthy children, 3=asymptomatic CD at enrollment, 4=asymptomatic children at followup, 6=symptomatic CD at enrollment, 7=asymptomatic CD at followup.

1=Healthy adults, 2=healthy children, 3=asymptomatic CD at enrollment, 4=asymptomatic children at followup, 6=symptomatic CD at enrollment, 7=asymptomatic CD at followup.

1=Healthy adults, 2=healthy children, 3=asymptomatic CD at enrollment,
4=asymptomatic children at followup, 6=symptomatic CD at enrollment,
7=asymptomatic CD at followup.

Followup visit

Fecal Calprotectin values in relation to patient symptom group
P=0.074, comparing Calprotectin O.D. value <0.5 between sx and asx Crohn's
1=symptomatic CD  0=asymptomatic CD at followup

US 10,626,460 B2

USE OF GLYCANS AND GLYCOSYLTRANSFERASES FOR DIAGNOSING/MONITORING INFLAMMATORY BOWEL DISEASE

CROSS-REFERENCE TO RELATED APPLICATIONS

This application is a national stage filing under 35 U.S.C. § 371 of International Application No. PCT/US2014/017630 entitled "USE OF GLYCANS AND GLYCOSYLTRANSFERASES FOR DIAGNOSING/MONITORING INFLAMMATORY BOWEL DISEASE", filed Feb. 21, 2014, which claims the benefit under 35 USC § 119(e) of the filing date of U.S. Provisional Application No. 61/767,500, filed Feb. 21, 2013. The entire contents of both referenced applications are incorporated by reference herein.

CROSS-REFERENCE TO RELATED APPLICATIONS

This application claims the benefit of the filing date of U.S. Provisional Application No. 61/767,500, filed Feb. 21, 2013. The entire contents of this referenced application are incorporated by reference herein.

FEDERALLY SPONSORED RESEARCH

This invention was made with government support under DK078392 awarded by the National Institutes of Health. The government has certain rights in the invention.

BACKGROUND OF THE INVENTION

Inflammatory bowel disease (IBD), including Intestinal Colitis, Crohn's Disease (CD) and Ulcerative Colitis (UC), involves chronic inflammation of all or part of the digestive tract. Intestinal Colitis involves non-specific inflammation of the intestine. CD involves inflammation anywhere along the lining of the digestive tract, while UC involves chronic inflammation in a subsection of the digestive tract and usually only affects the innermost lining of the colon and rectum. Onset of IBD occurs from early childhood to older adulthood and includes symptoms of bloody stool, diarrhea, severe abdominal cramps and pain, and weight loss.

IBD is a debilitating condition affecting an estimated 1.4 million Americans, and is a high public health priority. The incidence of IBD has been increasing in the general population. It is costly in health care utilization, lost productivity, and quality of life, with estimated costs for privately insured IBD patients ranging from $15,020 to $18,963 per year.

Currently available treatment for IBD includes a stepwise application of antibiotics, corticosteroids, and immune modifying treatments. However, not all patients respond to these regimes. The loss of clinical response is a challenge that results in further morbidity, reduced quality of life, and increased costs. To date, there is no validated approach for monitoring patient health status while under treatment. Considering the variability in patient response and the frequent occurrence of flares or relapse in disease, finding and validating novel approaches for patient monitoring and self-monitoring holds great promise for improving care as well as patient quality of life. It is therefore of great interest to develop new approaches for monitoring IBD development and progression.

SUMMARY OF THE INVENTION

The present disclosure is based on the unexpected discovery that levels of certain glycosyltransferases and/or the glycan antigens synthesized by these enzymes, e.g., the histo-blood group antigens, are associated with IBD and therefore can be used in IBD diagnosis and/or prognosis.

Accordingly, one aspect of the present disclosure provides a method for diagnosing IBD in a subject, the method (e.g., an in vitro method) comprising: (i) measuring a level of at least one glycosyltransferase in a tissue sample (for example, an intestinal sample, a colon biopsy sample, a biofluid sample, a saliva sample, or a stool sample) of a subject (e.g., a human subject) suspected of having inflammatory bowel disease (IBD); (ii) determining an expression profile of the at least one glycosyltransferase in the tissue sample; and (iii) assessing whether the subject has or is at risk for IBD (e.g., Intestinal Colitis, Ulcerative Colitis or Crohn's Disease) based on the expression profile of the least one glycosyltransferase. The at least one glycosyltransferase can be fucosyltransferase 3 (FUT3), fucosyltransferase 5 (FUT5), fucosyltransferase 7 (FUT7), ST3 beta-galactoside alpha-2,3-sialyltransferase 3 (ST3Gal III), ST3 beta-galactoside alpha-2,3-sialyltransferase 4 (ST3Gal IV), or a combination thereof.

In one example, the at least one glycosyltransferase includes one or more of FUT3, FUT5, FUT7, and ST3Gal III. When the tissue sample exhibits an expression profile representing a reduced level of the one or more of FUT3, FUT5, FUT7, or ST3Gal III as compared to a control sample, the subject is determined as having or being at risk for IBD.

In another example, the at least one glycosyltransferase includes ST3Gal IV. When the tissue sample exhibits an expression profile representing an elevated level of ST3Gal IV as compared with the expression profile of ST3Gal IV in a control tissue sample, the subject is determined as having or being at risk for IBD.

In yet another example, the at least one glycosyltransferase includes ST3Gal IV and one or more of FUT3, FUT5, FUT7, and ST3Gal III. If the tissue sample exhibits an expression profile representing an elevated level of ST3Gal IV and a reduced level of the one or more of FUT3, FUT5, FUT7, and ST3Gal III, the subject is determined as having or being at risk for IBD.

In any of the examples described above, the at least one glycosyltransferase can further include fucosyltransferase 2 (FUT2). For example, if the tissue sample exhibits an expression profile representing an elevated level of ST3Gal IV and a reduced level of the one or more of FUT2, FUT3, FUT5, FUT7, and ST3Gal III, the subject is determined as having or being at risk for IBD.

In any of the methods described above, the expression level of the at least one glycosyltransferase can be determined by measuring the mRNA level of the at least one glycosyltransferase in the tissue sample or by measuring the level of a microRNA that regulates the expression of the at least one glycosyltransferase. The mRNA and microRNA levels can be determined by PCR, in situ hybridization, RNA sequencing, or flow cytometry.

In a further aspect, the present disclosure provides a method for diagnosing Ulcerative Colitis in a subject (e.g., a human subject), the method comprising: (i) measuring an expression level of fucosyltransferase 2 (FUT2) in a tissue sample (for example, an intestinal sample, a colon biopsy sample, a biofluid sample, a saliva sample, or a stool sample) of a subject suspected of having Ulcerative Colitis (UC), and (ii) assessing whether the subject has or is at risk for UC based on the expression level of FUT2 in the tissue sample. When the tissue sample exhibits a reduced level of FUT2 as compared with that in a control tissue sample, the subject is determined as having or being at risk for UC. The expression profile of FUT2 can be determined by measuring the mRNA level of FUT2 or the level of a microRNA that regulates FUT2 expression. The mRNA and microRNA levels can be determined, for example, by PCR, in situ hybridization, RNA sequencing, or flow cytometry.

In another aspect, the present disclosure provides a method for diagnosing inflammatory bowel disease (IBD) in a human subject, the method comprising: (i) measuring a level of one or more histo-blood group antigens in a tissue sample (for example, an intestinal sample, a colon biopsy sample, a biofluid sample, a saliva sample, or a stool sample) of a human subject suspected of having IBD, (ii) determining an expression profile of the one or more histo-blood group antigens in the tissue sample, and (iii) assessing whether the human patient has or is at risk for IBD (e.g., Intestinal Colitis, Ulcerative Colitis or Crohn's Disease) based on the expression profile of the one or more histo-blood group antigens, which can comprise one or more of sialyl Lewis x ($sLe^x$), sialyl Lewis a ($sLe^a$), and Lewis b ($Le^b$). Optionally, the one or more histo-blood group antigen can further comprise an H antigen.

In one example, the histo-blood group antigen(s) examined in the methods described above is $sLe^x$, $sLe^a$, or both. In another example, the histo-blood group antigen(s) examined in the methods described above is $sLe^x$. If the tissue sample exhibits an expression profile representing an elevated level of the histo-blood group antigen(s), the human subject is determined as having or being at risk for IBD.

The above-noted histo-blood group antigen(s) can further comprise $Le^b$, and/or an H antigen. If the tissue sample exhibits a reduced level of H antigen as compared to that of a control sample, the human subject is further determined as having or being at risk for IBD.

In any of the methods described above where applicable, the level of the one or more histo-blood antigens can be measured by an immune assay, agglutination inhibition assay, or flow cytometry.

Any of the diagnosis methods described herein can further comprise administering to the subject an effective amount of an anti-IBD drug, if the subject is diagnosed as having or at risk for IBD, such as Intestinal Colitis, Ulcerative Colitis, or Crohn's Disease.

In yet another aspect, the present disclosure features a method for monitoring inflammatory bowel disease (IBD) progression in a subject (e.g., a human subject or a laboratory animal), the method comprising: (i) measuring a first expression level of at least one glycosyltransferase in a first tissue sample obtained from a subject having inflammatory bowel disease (IBD) at a first time point, and a second expression level of the at least one glycosyltransferase in a second tissue sample of the subject at a second time point, which is later than the first time point, (ii) determining a first expression profile of the at least one glycosyltransferase in the first tissue sample and a second expression profile of the at least one glycosyltransferase in the second tissue sample; and (iii) assessing IBD (e.g., Intestinal Colitis, Ulcerative Colitis or Crohn's Disease) progress in the subject based on the second expression profile as compared with the first expression profile. If there is a change between the first expression profile and the second expression profile, the subject is determined as having IBD progression or regression. The first and second tissue samples both can be an intestinal sample, a colon biopsy sample, a biofluid sample, a saliva sample, or a stool sample.

In some embodiments, the subject has undergone a treatment of IBD. In that case, the first and second tissue samples can be obtained before and after the treatment, respectively. Alternatively, at least one of the samples can be obtained during the course of the treatment. When necessary, the method described above further comprises assessing the efficacy of the treatment based on the second expression profile as compared with the first expression profile.

In one example, the at least one glycosyltransferase includes one or more of FUT3, FUT5, FUT7, and ST3Gal III. If the second expression profile represents a reduced level of the one or more of FUT3, FUT5, FUT7, and ST3Gal III as compared with the first expression profile, the subject is determined as having IBD progression. On the other hand, if the second expression profile represents an elevated level of the one or more of FUT3, FUT5, FUT7, and ST3Gal III as compared with the first expression profile, the subject is determined as having IBD regression.

In another example, the at least one glycosyltransferase includes ST3Gal IV. If the second expression profile represents an elevated level of ST3Gal IV as compared with the first expression, the subject is determined as having IBD progression. If the second expression profile represents a reduced level of ST3Gal IV as compared with the second expression profile, the subject is determined as having IBD regression.

Alternatively, the just-noted at least one glycosyltransferase further includes FUT2. When the at least one glycosyltransferase includes ST3GalIV and one or more of FUT2, FUT3, FUT5, FUT7, and ST3Gal III, if the second expression profile represents an elevated level of ST3Gal IV and a reduced level of the one or more FUT2, FUT3, FUT5, FUT7, and ST3Gal III as compared with the first expression profile, the subject is determined as having IBD progression. On the other hand, if the second expression profile represents a reduced level of ST3Gal IV and an elevated level of the one or more FUT2, FUT3, FUT5, FUT7, and ST3Gal III as compared with the first expression profile, the subject is determined as having IBD regression.

In any of the methods described above, the expression levels of the at least one glycosyltransferase is determined by measuring the mRNA levels of the at least one glycosyltransferase in the tissue samples or by measuring the levels of a microRNA that regulates the expression of the at least one glycosyltransferase. The mRNA and microRNA levels can be determined, for example, by PCR, in situ hybridization, RNA sequencing, or flow cytometry.

In yet another aspect, the present disclosure provides a method for monitoring Ulcerative Colitis (UC) progression in a subject, the method comprising: (i) determining a first expression level of fucosyltransferase 2 (FUT2) in a first tissue sample of a subject having UC at a first time point, and a second expression level of FUT2 in a second tissue sample of the subject at a second time point, which is later than the first time point, and (ii) and (ii) assessing UC progression in the subject based on the second expression level of FUT2 as compared with the first expression level of FUT2. If the second expression level of FUT2 is reduced as compared with the first expression level of FUT2, the subject is determined as having UC progression. If the second expression level of FUT2 is elevated as compared with the first expression level of FUT2, the subject is determined as having UC regression.

The expression level of FUT2 can be determined by measuring its mRNA level in the tissue sample or by measuring the level of a microRNA that regulates FUT2 expression. The mRNA and microRNA levels can be measured, for example, by PCR, in situ hybridization, RNA sequencing, or flow cytometry.

In some embodiments, the just-described method can involve taking samples from subjects having undergone a treatment of IBD. Either the first and second intestinal samples can be obtained before and after the treatment, respectively. Alternatively at least one of the samples is obtained during the course of the treatment. When desired, this method further comprises assessing the efficacy of the treatment based on the second expression profile as compared with the first expression profile.

In still another aspect, the present disclosure features a method (e.g., an in vitro method) for monitoring inflammatory bowel disease (IBD) progression in a human patient, the method comprising: (i) measuring a first level of one or more histo-blood group antigens in a first tissue sample of a human IBD patient at a first time point and a second level of the one or more histo-blood group antigens in a second tissue sample of the human patient at a second time point, which is later than the first time point, (ii) determining a first profile of the one or more histo-blood group antigens in the first tissue sample and a second profile of the one or more histo-blood group antigens in the second sample, and (iii) assessing IBD (for example, Intestinal Colitis, Ulcerative Colitis or Crohn's disease) progression or regression in the human patient based on the second profile of the one or more histo-blood antigens as compared with the first profile of the one or more histo-blood antigens. The one or more histo-blood group antigens can comprise one or more of sialyl Lewis x (sLe$^x$), sialyl Lewis a (sLe$^a$), and Lewis b (Le$^b$), and optionally an H antigen. In one example, the one or more histo-blood group antigens is sialyl Lewis x (sLe$^x$). The first and second tissue samples both can be an intestinal sample, a colon biopsy sample, a biofluid sample, a saliva sample, or a stool sample. The level of the one or more histo-blood antigens can be measured, for example, by an immune assay, agglutination inhibition assay, or flow cytometry.

In one example, the histo-blood group antigen(s) to be measured in the above method is sLe$^x$, sLe$^a$, or both. Optionally, the histo-blood group antigens further include Le$^b$, an H antigen, or both. The human subject is determined as having IBD progression if the second expression profile indicates elevated levels of the one or more histo-blood group antigens as compared with the first expression profile. Conversely, the human subject is determined as having IBD regression if the second profile indicates reduced levels of the one or more histo-blood group antigens as compared with the first profile.

When the histo-blood antigens include an H antigen, a human subject is determined to have IBD progression if the second profile indicates a reduced level of the H antigen and an elevated level of other histo-blood group antigens as compared with the first profile. Conversely, the human subject is determined to have IBD regression if the second profile indicates an elevated level of the H antigen and reduction of other histo-blood group antigens as compared with the first profile.

In another example, the level of an H antigen, either alone or in combination of any of the other glycan antigens described herein, of a test subject is measured to assess whether that subject has or is at risk for Ulcerative Colitis. If a reduced level of the H antigen is observed, the test subject is determined as having or being at risk for Ulcerative Colitis.

Also within the scope of this disclosure are kits for use in diagnosing IBD or monitoring IBD progression/regression in a subject, such as a human subject. Such a kit comprises reagents (e.g., oligonucleotides) for determining the level(s) of one or more of the glycosyltransferases described herein (e.g., FUT2, FUT3, FUT5, FUT7, ST3Gal III, and/or ST3Gal IV), or reagents (e.g., antibodies) for determining the levels of one or more histo-blood group antigens also described herein (e.g., sLe$^x$, sLe$^a$, Le$^b$, or an H antigen).

In addition, the present disclosure provides a method (e.g., an in vitro method) for monitoring Crohn's disease (CD) progression, the method comprising: (i) measuring a first level of one or more human blood group antigens in a first tissue sample of a human CD patient at a first time point and a second level of the one or more human blood group antigens in a second tissue sample of the human CD patient at a second time point, which is later than the first time point; (ii) determining a first profile of the one or more human blood group antigens in the first tissue sample and a second profile of the one or more human blood group antigens in the second tissue sample; and (iii) assessing CD progression or regression in the human patient based on the second profile as compared with the first profile; wherein the one or more human blood group antigens comprise sialyl Lewis x (sLe$^x$), Lewis x (Le$^x$), or both. In one example, the one or more human blood group antigens is sialyl Lewis x (sLe$^x$). The first and second tissue samples may both be intestinal samples, colon biopsy samples, biofluid samples, saliva samples, or stool samples. The subject may exhibit at least one symptom associated with CD. In one example, the subject is undergoing a CD treatment and the disease progression status as assessed by this method can be used to evaluate the efficacy of the treatment on the subject.

In some embodiments, the second profile representing an elevated level of the one or more human blood group antigens (e.g., an elevated level of sialyl Lewis x (sLe$^x$), Lewis x (Le$^x$), or both) as compared with the first profile indicates CD progression in the patient and the second profile representing a reduced level of the one or more human blood group antigens as compared with the first profile indicates CD regression in the patient.

In other embodiments, the levels of the one or more human blood antigens can be measured by an immune assay, agglutination inhibition assay, or flow cytometry.

Further, the present disclosure features a method (e.g., an in vitro method) for diagnosing Crohn's disease (CD), the method comprising: (i) measuring a level of one or more human blood group antigens in a tissue sample of a human subject suspected of having CD, (ii) determining a profile of the one or more human blood group antigens in the tissue sample, and (iii) assessing whether the human patient has or is at risk for CD based on the profile of the one or more human blood group antigens; wherein the one or more human blood group antigens comprise an H antigen, Lewis b (Le$^b$), Lewis y (Le$^y$), or a combination thereof. In some examples, the profile representing a decreased level of H antigen, Lewis b (Le$^b$), Lewis y (Le$^y$), or a combination thereof, indicates that the human subject has or is at risk for CD. In other examples, the tissue sample can be an intestinal sample, a colon biopsy sample, a biofluid sample, a saliva sample, or a stool sample. The level of the one or more human blood antigens is measured by an immune assay, agglutination inhibition assay, or flow cytometry.

A subject identified as having or at risk for CD by the methods described herein can be subjected to a treatment against CD, such as those described herein.

The details of one or more embodiments of the invention are set forth in the description below. Other features or advantages of the present invention will be apparent from the following drawings and detailed description of several examples, and also from the appended claims.

BRIEF DESCRIPTION OF THE DRAWINGS

The drawings are first described.

DETAILED DESCRIPTION OF THE INVENTION

Figure 1:
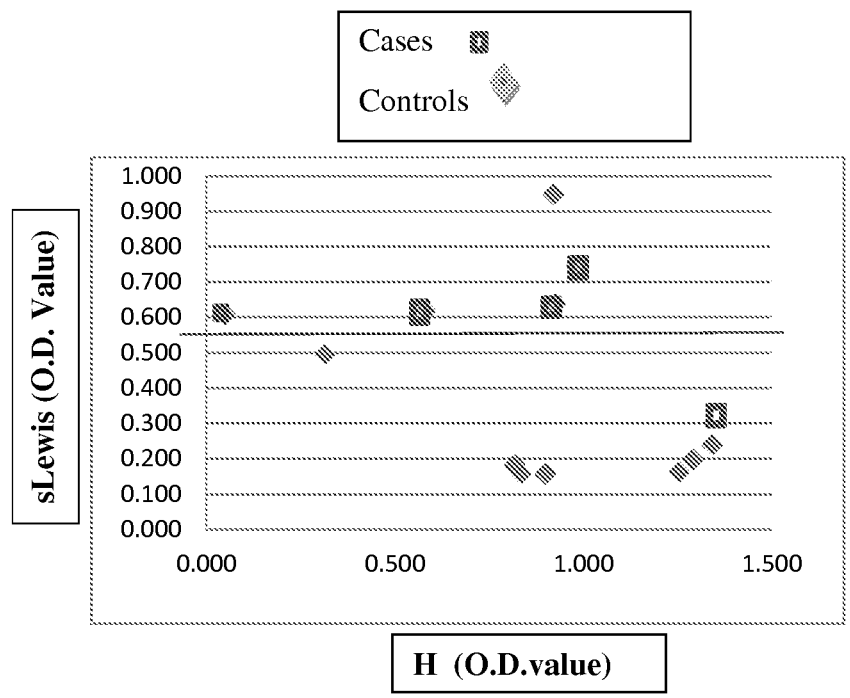
FIG. 1 is a scatterplot of sialyl Lewis and H antigen levels in cases/patients and controls. Boxes represent patients with IBD while diamonds represent controls. The solid line represents the cut-off value for significant differentiation between patients and controls.

Inflammatory bowel disease (IBD), including Intestinal Colitis, Crohn's Disease (CD) and Ulcerative Colitis (UC), involves chronic inflammation of all or part of the digestive tract. Onset of IBD occurs from early childhood to older adulthood and includes symptoms of bloody stool, diarrhea, severe abdominal cramps and pain, and weight loss.

The present disclosure is based on the unexpected discoveries that the levels of certain glycosyltransferases, including sialyltransferases (e.g., ST3Gal III, ST3Gal IV, ST6Gal 1, ST6Gal 2, and ST6GalNAc 1) and fucosyltransferases (e.g., FUT2, FUT3, FUT5, and FUT7), are associated with development of IBD. Thus, these glycosyltransferases, either taken alone or in combination, as well as their glycan products such as histo-blood group antigens (e.g., H antigens, Lewis antigens, and/or sialyl Lewis antigens) can be used as biomarkers for diagnosing IBD, assessing the risk for IBD development, or monitoring IBD progression/regression in a patient. Accordingly, described herein are methods for diagnosing IBD in a subject based on the expression profile of one or more glycosyltransferase, the expression profile of one or more histo-blood group antigens, or both; and methods for monitoring disease progression/regression of an IBD patient based on the just-noted expression profiles.

IBD Diagnosis

One aspect of the present disclosure relates to methods (e.g., in vitro methods) for diagnosing IBD in a subject (e.g., a human subject), including determining presence/absence of IBD in the subject and/or assessing the risk for developing IBD in the subject, based on the expression profile (level) of one or more glycosyltransferases.

Glycosyltransferases catalyze the transfer of a monosaccharide unit from an activated nucleotide sugar to a glycosyl acceptor molecule. Glycosyltransferases useful in the methods described herein include both fucosyltransferases (FUT) and sialyltransferases (ST), which are well-characterized enzymes involved in biosynthesis of histo-blood group antigens.

Fucosyltransferases catalyze the addition of fucose to precursor polysaccharides in the last step of histo-blood group antigen biosynthesis via different linkages. For example, FUT2 adds fucose residues to precursor polysaccharides in an alpha1,2-linkage and FUT3 adds fucose residues to precursor polysaccharides in an alpha1,3-linkage. Examples of fucosyltransferase genes to be used as biomarkers in the methods described herein include, but are not limited to, FUT2 (e.g., GenBank Accession Nos. NM_000511 and NM_001097638), FUT3 (e.g., GenBank Accession Nos. NM_000149, NM_001097639, NM_001097640, and NM_001097641), FUT5 (e.g., GenBank Accession No. NM_002034), and FUT7 (e.g., GenBank Accession No. NM_004479).

Sialyltransferases are involved in biosynthesis of sialyl Lewis antigens, including sialyl Lewis x ($sLe^x$), sialyl Lewis y ($sLe^y$), sialyl Lewis a ($sLe^a$), and sialyl Lewis b ($sLe^b$), through addition of sialic acid. Examples of sialyltransferase genes useful in the methods disclosed herein include, but are not limited to, ST3Gal III (e.g., GenBank Accession Nos. NM_174963, NM_174964, NM_174965, NM_174966, NM_174967, NM_174968, NM_174969, and NM_174970) and ST3Gal IV (e.g., GenBank Accession Nos. NM_006278, NM_001254757, NM_001254758, and NM_001254759), ST6Gal1 (NM_003032.2, NM_173216.2, NM_173217.2), ST6Gal2 (NM_001142351.1, NM_001142352.1, NM_032528.2) and ST6GalNAc1 (NM_018414.3).

To practice this method, the level(s) of one or more of the glycosyltransferases noted above in a tissue sample of a candidate subject can be determined by performing a method known in the art or based on medical records of that candidate subject. In one example, a tissue sample (e.g., saliva, intestinal biopsy, colon biopsy, biofluid, or stool) can be obtained from a subject (e.g., a human subject who can be suspected of having IBD) and the expression level of one or more of the glycosyltransferases described herein can be measured by conventional methods. In some embodiments, the expression level of one glycosyltransferase, e.g., selected from those noted above, such as ST3Gal IV or FUT3, is measured and used as a marker in the methods described herein. In other embodiments, a combination of glycosyltransferases, e.g., selected from those noted above, are examined and their expression pattern is used as a marker in the methods described herein. Any combination of the above noted glycosyltransferases can be used here. Specific examples include, but are not limited to, (a) ST3Gal IV and one of the fucosyltransferases FUT2, FUT3, FUT5, and FUT7; (b) ST3Gal III and ST3GalIV; or (c) ST3Gal III and one or more of FUT2, FUT3, FUT5, and FUT7.

In one example, the expression levels of the glycosyltransferases are determined by measuring the mRNA levels of the enzymes via, e.g., quantitative PCR (real-time PCR) or microarray hybridization. In another example, the levels of the glycosyltransferases can be determined by measuring the level(s) of one or more microRNAs that regulate the expression of these glycosyltransferases. Levels of microRNAs can be determined via a routine method, e.g., real-time PCR. Alternatively, the levels of these glycosyltransferases can be determined by measuring their protein levels via, e.g., immunoassays or by examining their enzymatic activities. Methods for determining RNA levels and protein levels are all well known in the art, including hybridization, PCR, ELISA, sequencing, agglutination inhibition assay, and flow cytometry. See, e.g., Molecular Cloning: A Laboratory Manual, J. Sambrook, et al., eds., Third Edition, Cold Spring Harbor Laboratory Press, Cold Spring Harbor, N. Y., 2001, Current Protocols in Molecular Biology, F. M. Ausubel, et al., eds., John Wiley & Sons, Inc., New York. Microarray technology is described in Microarray Methods and Protocols, R. Matson, CRC Press, 2009, or Current Protocols in Molecular Biology, F. M. Ausubel, et al., eds., John Wiley & Sons, Inc., New York. Methods for determining the activity of a glycosyltransferase as described herein, e.g., FUT2, are also well known in the art. See, e.g., U.S. Pat. No. 7,871,785, which is incorporated by reference herein.

The data thus obtained can be normalized against the expression level of an internal control RNA (e.g., a ribosomal RNA or U6 RNA). The normalized expression level(s) of the glycosyltransferase(s) can then be compared to the expression level(s) of the same glycosyltransferase(s) of a control tissue sample, which can be normalized against the same internal control RNA, to determine whether the subject has or is at risk for developing IBD (having a higher probability of IBD occurrence as compared to a normal subject).

The control tissue sample can be obtained from a subject free of IBD. Alternatively, the control tissue sample can be obtained from a pool of IBD-free subjects. Optionally, these IBD-free subjects match with the test subject in, e.g., age, gender, and/or ethnic background. Preferably, the control tissue sample and the tissue sample examined in the methods described here are of the same type. When an intestinal biopsy or colon biopsy sample is used, the control tissue sample can be obtained from the same subject but from an area free of inflammation.

When necessary (e.g., when more than one glycosyltransferase is investigated), the expression levels of the glycosyltransferases (preferably normalized against an internal control RNA) can be processed by, e.g., a computational program to generate an expression profile (e.g., an mRNA signature), which can be represented by a number or numbers, that characterize the expression pattern of the glycosyltransferases. The expression levels of these glycosyltransferases from the control tissue sample can be processed by the same method to generate an expression profile representing the expression pattern of these glycosyltransferases of the control. The expression profile (mRNA signature) of the test subject can be compared with the expression profile of the control sample to determine whether the subject has or is at risk for IBD development.

Various computational programs can be applied in the methods of this disclosure to aid in analysis of expression data. Examples include, but are not limited to, Prediction Analysis of Microarray (PAM; see Tibshirani et al., PNAS 99(10):6567-6572, 2002); Plausible Neural Network (PNN; see, e.g., U.S. Pat. No. 7,287,014), PNNSulotion software and others provided by PNN Technologies Inc., Woodbridge, Va., USA, and Significance Analysis of Microarray (SAM).

As described herein, elevated levels of ST3Gal IV and a reduced level of FUT2, FUT3, FUT5, FUT7, or ST3Gal III were found to be associated with IBD development, including the occurrence of both Crohn's Disease and Ulcerative Colitis. Thus, if the expression profile of one or more of the above-noted glycosyltransferases of a test subject, relative to that of a control subject, represents an elevated level of ST3Gal IV, and/or a reduced level of one or more of FUT2, FUT3, FUT5, FUT7, and ST3Gal III, the test subject is determined to have or be at risk for IBD (e.g., Intestinal Colitis, Crohn's Disease or Ulcerative Colitis).

In one example, the expression profile of FUT2, either alone or in combination of any of the other glycosyltransferases described herein, of a test subject is determined to assess whether that subject has or is at risk for Ulcerative Colitis. If the expression profile represents a reduced level of FUT2, the test subject is determined as having or being at risk for Ulcerative Colitis.

In another example, the expression profile of FUT2, either alone or in combination of any of the other glycosyltransferases described herein, in a saliva sample of a test subject is determined to assess whether that subject has or is at risk for IBD. If the expression profile represents a reduced level of FUT2, the test subject is determined as having or being at risk for Ulcerative Colitis.

In another example, the expression profile of FUT2, either alone or in combination of any of the other glycosyltransferases described herein, in a saliva sample of a test subject is determined to assess whether that subject has or is at risk for IBD. If the expression profile represents a reduced level of FUT2, the test subject is determined as having or being at risk for IBD.

In another aspect, the present disclosure relates to methods for diagnosing IBD (e.g., diagnosing UC or CD) in a subject (e.g., a human subject), including determining presence/absence of IBD in the subject and/or assessing the risk for developing IBD in the subject, based on the expression profile of one or more glycans that are products of one or more of the glycosyltransferases noted above, including histo-blood group antigens. Human histo-blood group antigens are a set of innate, fucosylated carbohydrates expressed on red blood cells, in saliva, on epithelial surfaces, and on intestinal mucosa. Examples include, but are not limited to, H antigens (H1 and H2), Lewis antigens (Lewis a or $Le^a$; Lewis b or $Le^b$; Lewis x or $Le^x$; and Lewis y or $Le^y$), and sialyl Lewis antigens such as sialyl Lewis a ($sLe^a$), sialyl Lewis b ($sLe^b$), sialyl Lewis x ($sLe^x$), and sialyl Lewis y ($sLe^y$).

Histo-blood group antigens can act as cell binding sites for both cells of the immune system and for microbial organisms, either commensal or pathogenic (Henry 2001). Polymorphisms in certain fucosyltransferase genes are known to determine expression of the Lewis blood-group type, fucosylated oligosaccharide patterns in human milk, and histo-blood group antigens on human epithelial cell surfaces (Niverge et al 1990, Thurl et al 1997, Chaturvedi et al 2001). Thus, like the glycosyltransferases discussed herein, glycan products of these glycosyltransferases such as histo-blood group antigens can also be used as biomarkers in the methods described herein.

In some embodiments, a single glycan antigen from those described herein (e.g., $sLe^x$, $Le^x$, H, $Le^b$, $Le^y$, and $sLe^a$) is used as an IBD marker. In other embodiments, a combination of the glycan antigens described herein is used as an IBD marker, e.g., any combination of the histo-blood group antigens described above. Examples include, but are not limited to, (a) $sLe^x$ and $Le^b$, (b) $sLe^a$ and $Le^b$, (c) $sLe^x$ and one or more of H, $Le^a$, $Le^b$, $Le^x$, and $Le^y$, (d) $sLe^a$ and one or more of H, $Le^a$, $Le^b$, $Le^x$, and $Le^y$, (e) $sLe^x$ and $Le^x$, (f) H and one or more of $sLe^x$, $Le^b$, and $sLe^a$, and (g) at least two of H, $Le^b$, and Le.

The levels of these glycan antigens can be measured by routine practice, e.g., by an immunoassay such as ELISA or using lectins such as UEA1, AIA, GSA II, WGA, sWGA, SNA, MAL-II, PWA, SJA, LEA, and I-PHA. Other methods for determining the levels of glycan antigens such as histo-blood group antigens include, but are not limited to, flow cytometry, and agglutination inhibition assay.

The level(s) of the glycan antigen(s) thus obtained can be normalized and optionally processed following the procedures described above to generate an expression profile, which is then compared with that of a control sample to determine whether a test subject has or is at risk for IBD. In one example, the expression profile of $sLe^x$, $sLe^a$, or both is determined and if the expression profile obtained from a tissue sample of the test subject represents an elevated level of $sLe^x$, $sLe^a$, or both, the test subject is determined as having or being at risk for IBD. When desired, the level of $Le^b$, an H antigen, or both can also be determined. In that case, if an expression profile represents a reduced level of the H antigen, and/or an elevated level of $Le^b$, the test subject is determined as having or being at risk for IBD.

In one example, the level of an H antigen, either alone or in combination of any of the other glycan antigens described herein, of a test subject is determined to assess whether that subject has or is at risk for Ulcerative Colitis. If the expression profile represents a reduced level of the H antigen, the test subject is determined as having or being at risk for Ulcerative Colitis.

The above-described methods can be applied to a test subject, which can be a human subject, e.g., a non-secretor human subject (an individual who secretes a low level or no blood group antigens into body fluids). In one example, the human subject is suspected of having IBD. A subject suspected of having IBD may show one or more symptoms associated with IBD, e.g., abdominal pain, vomiting, diarrhea, rectal bleeding, severe internal cramps/muscle spasms in the region of the pelvis, and/or weight loss, or may be asymptomatic but exhibit one or more risk factors associated with IBD. IBD-associated risk factors include genetic factors (specific gene mutations), environmental factors (IBD is more common in developed countries, urban areas, and colder climates, and among people with high socioeconomic status), age (onset is usually between the ages of 15 and 35), race (Caucasians have the highest risk), family history, use of nonsteroidal anti-inflammatory drugs (e.g., ibuprofen), smoking, and lack of breast-feeding.

In another example, the level of $Le^b$, $Le^y$, an H antigen, or a combination thereof can be used to diagnose CD. A reduced level of one or more of these antigens is indicative of presence or risk of the disease.

IBD Prognosis

Any of the glycosyltransferases, combinations thereof, or human histo-blood group antigens, and combinations thereof as described herein can also be used as prognostic markers to monitor the status of IBD (including Intestinal Colitis, Crohn's disease and Ulcerative Colitis), including progression and regression, in a subject, which can be a human subject or a laboratory animal. Accordingly, also disclosed herein are prognostic methods for monitoring the disease status of a subject based on changes in the levels of one or more glycosyltransferases or changes of the levels of one or more histo-blood group antigens of a subject. Optionally, this method can be practiced during the course of an IBD treatment to assess the efficacy of the treatment in a subject.

To practice this method, tissue samples (e.g., saliva, intestinal biopsy, colon biopsy, biofluid, or stool) can be collected via routine methods at various time points (e.g., along the course of a treatment) from a subject, who has or is suspected of having IBD. The expression level(s) of a glycosyltransferase (e.g., ST3Gal IV or FUT3), a combination of glycosyltransferases (e.g., ST3Gal IV and one or more of FUT2, FUT3, FUT5, FUT7, and ST3Gal III), a histo-blood group antigen (e.g., $sLe^x$ or $sLe^a$) or a combination of the blood group antigens (e.g., $sLe^x$ or $sLe^a$ and one or more of H antigen and $Le^b$) can be measured as described above. The levels of the one or more glycosyltransferases or the levels of the one or more histo-blood group antigens thus obtained can be normalized and optionally processed following the procedures described above to generate an expression profile of the sample obtained at each time point.

The expression profile of a sample obtained from a later time point is compared with that of a sample obtained from an earlier time point. If there is a change between the two expression profiles, the subject is determined to have IBD progression or regression. For example, if a change of the expression profile represents an increased level of a glycosyltransferase (e.g., ST3Gal IV) or a histo-blood group antigen that is correlated with IBD ($sLe^x$, $sLe^a$, or $Le^b$) develop along the course, or if the change of the expression profile represents a decreased level of a glycosyltransfearse (e.g., FUT2, FUT3, FUT5, FUT7, or ST3Gal III) or a histo-blood group antigen (e.g., H1 or H2) that is inversely correlated with IBD development, the subject is determined as having IBD progression. On the other hand, if a change of the expression profile represents a decreased level of a glycosyltransferase (e.g., ST3Gal IV) or a histo-blood group antigen that is correlated with IBD ($sLe^x$, $sLe^a$, or $Le^b$) develop along the course, or if the change of the expression profile represents an increased level of a glycosyltransfearse (e.g., FUT2, FUT3, FUT5, FUT7, or ST3Gal III) or a histo-blood group antigen (e.g., H) that is inversely correlated with IBD development, the subject is determined to have IBD regression.

When the above method is performed on an IBD patient undergoing a treatment, a first tissue sample or a first set of tissue samples can be collected at a time point before the treatment begins and a second sample or a set of samples is collected from a subject at a later time point than the first time point, e.g., during or after treatment. If necessary, multiple samples/sample sets can be collected along the course of the treatment. The expression profile(s) of the glycosyltransferase(s) and/or histo-blood group antigen(s) can be determined as described herein and the disease progression/regression can be assessed based on changes of the expression profiles along the course of the treatment (that is, changes of the expression profile in samples taken at intervals later in the course of the treatment as compared to those in samples taken at intervals earlier in the course of the treatment). For example, if changes in the expression profile represent an increased level of ST3Gal IV or $sLe^x$ and/or $sLe^a$, or a decreased level of FUT2, FUT3, FUT5, FUT7, or ST3Gal III, the patient is determined to have IBD progression during the course of the treatment. In that case, the treatment is determined as have little or no effect on the patient. On the other hand, if changes in the expression profile represent a decreased level of ST3Gal IV or $sLe^x$ and/or $sLe^a$, or an increased level of FUT2, FUT3, FUT5, FUT7, or ST3Gal III, the patient is determined to have IBD regression during the course of the treatment. In that case, the treatment is determined as being effective on the patient.

In some embodiments, the expression profile of FUT2, either alone or in combination of any of the other glycosyltransferases described herein, and/or the expression profile of an H antigen, either alone or in combination with any of the other histo-blood group antigens described herein, in a subject having is determined to assess disease status in that subject over time. If the expression profile of a later time point represents a reduced level of FUT2 or the H antigen as compared to that of an earlier time point, the subject is determined as having Ulcerative Colitis progression. Conversely, if the expression profile of a later time point represents an elevated level of FUT2 or an H antigen compared to the expression profile of an earlier time point, the subject is determined as having regression of Ulcerative Colitis.

In one example, the level of $sLe^x$, $Le^x$, or a combination thereof is used as a marker for assessing progression of Crohn's disease (CD). In another example, the level of $sLe^x$ is used as a marker for assessing progression of Crohn's disease (CD). An elevated level of $sLe^x$, $Le^x$, or both can be indicative of disease progress. Alternatively, a reduced level of one or both antigens can be indicative of disease regression. These two markers, either alone or in combination, are particularly useful in monitoring CD progression in human patient who exhibits at least one symptom associated with CD, e.g., abdominal pain, diarrhea (which may be bloody if inflammation is severe), vomiting, or weight loss, as well as complications outside the gastrointestinal tract such as anemia, skin rashes, arthritis, inflammation of the eye, tiredness, and lack of concentration.

Any of the diagnostic and prognostic methods described herein can further comprising subjecting the subject to an IBD treatment or adjusting the current IBD treatment that was applied to the subject.

Any of the above-described diagnosis or prognosis methods can be applied to a test subject, which can be a human subject as described above or a laboratory animal (e.g., a mouse, a rat, a guinea pig, a rabbit, a goat, or a non-human primate). For example, a subject may be a human known to have or suspected of having IBD. Further, this human may be in the process of or planning to undergo treatment of IBD. A subject may also be, e.g., an animal disease model of IBD. Treatment of subjects with or suspected of having IBD can include, but is not limited to, medications (e.g. corticosteroids, aminosalicylates, immunomodulators, antibiotics, and biologics), surgery (e.g. Ileoanal anastomosis, proctocolectomy with ileostomy, and strictureplasty), nutritional restrictions, and/or any other IBD treatment described herein.

IBD Treatment

When a subject is diagnosed by any of the methods described herein as having or at risk for developing IBD, this subject could be subjected to a treatment for IBD, including any of the IBD treatments known in the art and disclosed herein. For example, medications such as sulfasalazine (Azulfadine), mesalamine (Asacol, Pentasa), azathioprine (Imuran), 6-MP (Purinethol), cyclosporine, methotrexate, infliximab (Remicade) and corticosteroids (prednisone) can be administered to the subject in an amount effective to treating IBD (e.g., UC or CD). In some embodiments, the IBD treatment (e.g., UC or CD treatment) comprises an anti-inflammatory agent, an immune suppressant agent, an antibiotic agent, or a combination thereof. Non-limiting examples of anti-inflammatory agents include sulfasalazine, mesalamine, balsalazide, olsalazine, or corticosteroids (e.g., prednisone or budesonide). Non-limiting examples of immune suppressant agents include azathioprine, mercaptopurine, cyclosporine, infliximab, adalimumab, certolizumab pegol, methotrexate, or natalizumab. Non-limiting examples of antibiotics include metronidazole and ciprofloxacin. In some embodiments, IBD treatment comprises an anti-diarrheal (e.g., psyllium powder, methylcellulose or loperamide), a laxative, acetaminophen, iron, vitamin B-12, calcium, or vitamin D. In some embodiments, IBD treatment (e.g., UC or CD treatment) comprises surgery or fecal bacteriotherapy (also called a fecal microbiota transplantation or stool transplant). Non-limiting examples of surgery include proctocolectomy, ileostomy, or strictureplasty. In some embodiments, IBD treatment (e.g., UC or CD treatment) comprises a therapeutic agent (e.g., an anti-inflammatory agent, an immune suppressant agent, an antibiotic agent, or a combination thereof) and surgery. It is to be understood that any of the IBD treatments described herein may be used in any combination. The term "treating" as used herein refers to the application or administration of a composition including one or more active agents to a subject, who has IBD, a symptom of IBD, or a predisposition toward IBD, with the purpose to cure, heal, alleviate, relieve, alter, remedy, ameliorate, improve, or affect the disease, the symptoms of the disease, or the predisposition toward the disease. An "effective amount" is that amount of an anti-IBD agent that alone, or together with further doses, produces the desired response, e.g. eliminate or alleviate symptoms, prevent or reduce the risk of flare-ups (maintain long-term remission), and/or restore quality of life. The desired response is to inhibit the progression of the disease. This may involve only slowing the progression of the disease temporarily, although more preferably, it involves halting the progression of the disease permanently. This can be monitored by routine methods or can be monitored according to diagnostic and prognostic methods discussed herein. The desired response to treatment of the disease or condition also can be delaying the onset or even preventing the onset of the disease or condition.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Any of the methods described herein can further comprise adjusting the IBD treatment performed to the subject based on the results obtained from the diagnostic/prognostic method. Adjusting treatment includes, but are not limited to, changing the dose and/or administration of the anti-IBD agent used in the current treatment, switching the current medication to a different anti-IBD agent, or applying a new IBD therapy to the subject, which can be either in combination with the current therapy or replacing the current therapy.

In some embodiments, the present disclosure provides a method for treating a subject (e.g., a human patient) having inflammatory bowel disease (IBD), the method comprising administering an effective amount of an IBD drug such as those described herein (e.g., an anti-inflammatory agent, an immune suppressant agent, an antibiotic agent, or a combination thereof) to the subject, who exhibits an expression profile or expression level of at least one glycosyltransferase that deviates from a control. The at least one glycosyltransferase can comprises one or more of fucosyltransferase 3 (FUT3), fucosyltranferase 5 (FUT5), or fucosyltransferase 7 (FUT7), ST3 beta-galactoside alpha-2,3-sialyltransferase 3 (ST3Gal III), and ST3 beta-galactoside alpha-2,3-sialyltransferase 4 (ST3Gal IV). In one example, the subject has an elevated level of ST3Gal IV, a reduced level of the one or more of FUT3, FUT5, FUT7, and ST3Gal III, or both as compared to a control. Alternatively or in addition, the subject can further exhibit a reduced level of fucosyltransferase 2 (FUT2) as compared to a control.

In other embodiments, the present disclosure features methods for treating a human subject having inflammatory bowel disease (IBD), the method comprising administering an effective amount of an IBD drug (e.g., an anti-inflammatory agent, an immune suppressant agent, an antibiotic agent, or a combination thereof) to a subject having or at risk for IBD (e.g., a human patient). The subject exhibits a level or profile of one or more human blood group antigens that deviates from a control. The one or more human blood group antigens comprise one or more of sialyl Lewis x (sLe$^x$), sialyl Lewis a (sLe$^a$), and Lewis b (Le$^b$). In one example, the subject has an elevated level of sLe$^x$, sLe$^a$, or both as compared to a control. Alternatively or in addition, the subject exhibits a reduced level of H antigen compared to a control.

In yet other embodiments, provided herein are methods for treating a subject having Ulcerative Colitis (UC), the method comprising administering an effective amount of an anti-UC agent (e.g., an anti-inflammatory agent, an immune suppressant agent, an antibiotic agent, or a combination thereof) to a subject having UC, wherein the subject exhibits an expression level of fucosyltransferase 2 (FUT2) that is reduced as compared to a control. Such methods can further comprise monitoring the subject for UC progression by a suitable method as those described herein.

In addition, the present disclosure provides a method for treating a subject having Crohn's disease (e.g., a human patient), the method comprising administering an effective amount of an CD drug (e.g., an anti-inflammatory agent, an immune suppressant agent, an antibiotic agent, or a combination thereof) to the subject having or at risk for CD, wherein the subject has an expression profile of one or more human blood group antigens that deviates from a control. In one example, the one or more human blood group antigens comprise one or more of sialyl Lewis x (sLe$^x$), Lewis x (Le$^x$), H antigen, Lewis b (Le$^b$), and Lewis y (Le$^y$). In one example, the subject is a human patient exhibiting an elevated level of sLe$^x$, Le$^x$, or both as compared to a control. In another example, the subject is a human patient having a decreased level of H antigen, Le$^b$, Le$^y$, or a combination thereof, as compared to a control. Such methods can further comprise monitoring the subject for CD progression by a suitable method such as those described herein. In another example, the one or more human blood group antigens comprise sialyl Lewis x (sLe$^x$). In one example, the subject is a human patient exhibiting an elevated level of sLe$^x$ as compared to a control.

The subject to be treated by any of the treatment methods described herein can be identified as having or at risk for IBD by any of the methods described herein. The treatment methods as just described herein can further comprise monitoring the subject for IBD progression by a method of any one of the methods described herein. Based on the status of disease progression, a suitable IBD treatment can be applied to the subject.

Kits for Use in IBD Diagnosis and/or Prognosis

Also within the scope of this disclosure are kits for use in diagnosing IBD or monitoring IBD progression/regression in a subject, such as a human subject. Such a kit can comprise reagents for determining the level(s) of one or more of the biomarkers to be used in the diagnostic or prognostic methods described herein.

The kit noted above can comprise one or more reagents for determining the levels of one or more glycosyltransferases (e.g., FUT2, FUT3, FUT5, FUT7, ST3Gal III, and/or ST3Gal IV). The reagents can be oligonucleotide probes/primers for determining the mRNA levels of the one or more glycosyltransferases, or oligonucleotide probes/primers for examining the levels of one or more microRNAs that regulate the expression of these enzymes. Alternatively, the kit can contain antibodies specific to one or more of these enzymes. In one example, the kit comprises reagents for determining the levels of ST3Gal IV and one of the fucosyltransferases FUT2, FUT3, FUT5, and FUT7. In another example, the kit comprises reagents for determining the levels of ST3Gal III and ST3GalIV. In yet another example, the kit comprises reagents for determining the levels of ST3Gal III and one or more of FUT2, FUT3, FUT5, and FUT7. Alternatively, the kit comprises reagents for determining the levels of ST3Gal IV and one or more of FUT2, FUT3, FUT5, and FUT7.

When glycan markers are to be examined in the diagnostic/prognostic methods described herein, the kit can comprise one or more antibodies binding to the glycan markers (e.g., antibodies binding to $sLe^x$, $Le^x$, $sLe^a$, $Le^b$, $Le^y$ or H antigen) or one or more lectins binding to these glycan markers. In one example, the kit comprises one or more antibodies or lectins that bind to $sLe^x$.

Any of the kits described herein can further comprise an instruction manual providing guidance for using the kit to perform the diagnostic/prognostic methods.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Identification of Glycosyltransferases Differentially Expressed in Patients with IBD RNA samples were prepared from colon biopsies of affected segments of CD and UC patients and healthy controls, and the global patterns of gene expression were examined using the HGU133 Plus V.2 Affymetrix GeneChip in the Cincinnati Children's Digestive Health Center Microarray core.

As shown in Table 1, ST3Gal IV was found to be significantly ($p<0.01$) overexpressed in IBD patients versus controls. ST3Gal III and the fucosyltransferase genes, FUT2, FUT3, FUT5 and FUT7 were found to be significantly under-expressed ($p<0.05$) in IBD patients versus controls. The above results indicate that the expression level of any of these enzymes, or any combination thereof, can be used as a marker for diagnosing IBD or monitoring disease progress.

TABLE 1

Intestinal epithelial cell expression of fucosyltransferase genes and sialyltransferase genes from colon biopsy

| Gene expression | FUT2 | FUT3 | FUT5 | FUT7 | ST3Gal III | ST3Gal IV |
|---|---|---|---|---|---|---|
| Crohn's Disease N = 29 | 0.72 * | 0.59 + | 0.8 * | 0.73 * | 0.82 | 2.3 + |
| Ulcerative Colitis N = 8 | 0.58 * | 0.45 + | 0.8 * | 0.82 | 0.73 + | 2.9 + |

Compared to Controls (N = 8) as reference (1.0).
* $p \leq 0.05$,
+ $p \leq 0.01$ Example 2: Identification of Histo-Blood Group Antigens Differentially Expressed in Patients with IBD Saliva specimens were tested for secretor and Lewis types by monoclonal antibody based phenotyping methods as previously described. See Huang et al., J Infect Dis 2003; 188; 19-31. Briefly, boiled saliva samples were coated on microtiter plates (Dynex, Immulon; Dynatech, Franklin, Mass.) and then interacted with monoclonal antibodies specific to individual human blood group antigens. The bound antibodies were then detected by corresponding secondary antibody-horseradish peroxidase (HRP) conjugates followed by adding HRP substrate reagents (optEIA, BD Bioscience, San Diego, Calif.).

As shown in FIG. 1 and Table 2, the level of sialyl Lewis (sLewis) antigens, which refers to the average of $sLe^x$ and $sLe^a$ levels, was found to be significantly higher in IBD patients (i.e., cases) as relative to the controls.

TABLE 2

Optical density (OD) values for sialyl Lewis in patients with Crohn's Disease (CD) or (UC) or controls.

| sLewis O.D. values | |
|---|---|
| Case | Control |
| 0.24 CD | 0.16 asx Crohn's |
| 0.61 UC | 0.16 |
| 0.62 UC | 0.16 |
| 0.64 CD | 0.18 |
| 0.75 UC | 0.2 |
|  | 0.5 |
|  | 0.95 | setting sLewis cutpoint for O.D. value >0.5: Cases 4/5 (80%) vs Controls 1/7 (14%), p = 0.07
One control (asx Crohn's) was an asymptomatic Crohn's Disease patient.

Figure 2:
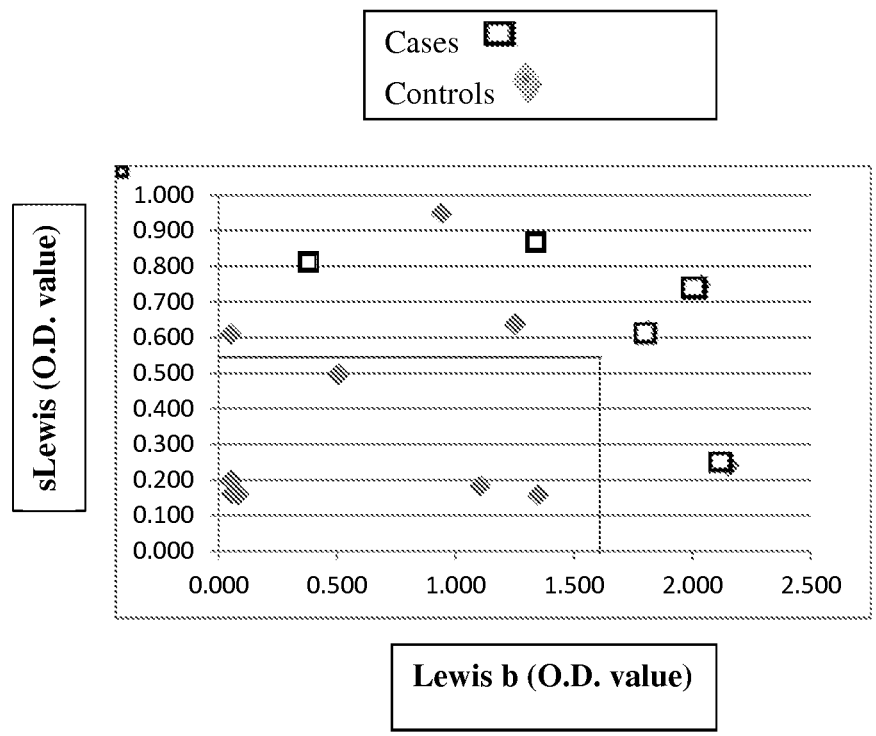
FIG. 2 is a scatterplot of sialyl Lewis and Lewis b antigen levels in cases/patients and controls. Boxes represent patients with IBD while diamonds represent controls. The solid lines represent the cut cut-off values for sialyl Lewis and Lewis b for significant differentiation between patients and controls.

FIG. 2 shows that all five IBD patients showed elevated sialyl Lewis levels (O.D.>0.5), elevated levels of Lewis b (O.D.>1.5), or both, while only one out of seven controls showed similar results (p=0.015, Fisher's exact). These data indicate that Lewis b can be used as an adjunct marker with sLewis for IBD diagnosis and/or prognosis.

Example 3: Salivary Glycan Biomarkers for Monitoring Crohn's Patients

The goal of this study was to study salivary glycans (histo-blood group antigens) as biomarkers of symptom flares in Crohn's Disease by examining the levels of these antigens in the saliva samples of symptomatic Crohn's disease patients, compared to asymptomatic Crohn's Disease patients and healthy controls. For the symptomatic and asymptomatic Crohn's Disease patients, a stool sample was also collected after the clinic visit, which was tested for fecal biomarkers. A second saliva sample was collected from the patient concurrent with the stool sample collection. It was determined that the primary candidate biomarker was sialyl Lewis x, as it was found to be elevated in symptomatic patients.

It was found that salivary levels of sialyl Lewis x antigen (and Lewis x antigen) were elevated in symptomatic Crohn's patients compared to the asymptomatic Crohn's patients in the second saliva collection. There was no association with these or other histo-blood group antigens in the first sample, taken at the time of a clinic visit for treatment. It is hypothesized that this anomalous finding is a treatment effect: That when initially enrolled and measured, the symptomatic Crohn's patients had already initiated treatment with medications that worked to reduce their inflammation. An additional piece of suggestive evidence was that salivary Lewis x was significantly elevated in individuals with a history of antibiotic use, including in controls.

Methods

Patient Enrollment

A total of 60 healthy control subjects were enrolled, of whom 30 were pediatric (11 to 17 years) and 30 were adults (18 to 55 years). A total of 20 asymptomatic Crohn's subjects were enrolled, ranging from 11 to 19 years of age. Subjects were recruited at a semi-annual visit that was scheduled to administer Infliximab (Remicade) in order to maintain remission in these subjects. The frequency of their clinic visits was individualized based on their history and scheduled to avoid symptom recurrence. At the time of enrollment, some subjects were awaiting treatment, but most had just initiated treatment. A total of 9 symptomatic Crohn's subjects were enrolled, ranging from 12 to 18 years of age. Three of these symptomatic patients were recruited as hospital inpatients, while six were recruited as outpatients who were experiencing a symptomatic flare. A detailed summary of the demographic characteristics of these patients is provided as Table 3.

TABLE 3

Patient Demographic Data.

| Question on Demograhic Form | Symptomatic Crohn's Disease Patients (n = 9) | Asymptomatic Crohn's Disease Patients (n = 20) | Pediatric Healthy Controls (n = 30) | Adult Healthy Controls (n = 30) |
|---|---|---|---|---|
| Weight (pounds) (mean ± SD) | 117.6 ± 14.48 | 129.8 ± 39.01 | 130.1 ± 34.68 | 187.5 ± 48.1 |
| Height (inches) (mean ± SD) | 64.7 ± 4.09 | 63.6 ± 4.56 | 64.43 ± 3.70 | 68.5 ± 3.66 |
| Health insurance? | | | | |
| Yes | 8 (88.8%) | 20 (100%) | 29 (96.6%) | 27 (90%) |
| No | 1 (11.1%) | 0 | 1 (3.3%) | 3 (10%) |
| Type of health insurance | | | | |
| Private | 8 (88.8%) | 14 (70%) | 24 (80%) | 24 (80%) |
| Public | 0 | 5 (25%) | 5 (16.6%) | 3 (10%) |
| Both | 0 | 1 (5%) | 0 | 0 |
| Unknown | 0 | 0 | 0 | 0 |
| Hispanic or Latino/a? | | | | |
| Yes | 0 | 1 (5%) | 0 | 4 (13.3%) |
| No | 8 (88.8%) | 19 (95%) | 30 (100%) | 26 (86.6%) |
| Race | | | | |
| White | 8 (88.8%) | 17 (85%) | 21 (70%) | 20 (66.6%) |
| Black, African-American | 1 (11.1%) | 3 (15%) | 10 (33.3%) | 10 (33.3%) |
| American Indian/Alaskan Native | 1 (11.1%) | 2 (10%) | 6 (20%) | 1 (3.3%) |
| Asian or other | 1 (11.1%) | 0 | 0 | 0 |
| Highest degree or diploma completed (if <18 years old: mother, if adult controls - themselves) | | | | |
| None | 0 | 2 (10%) | 0 | 1 (3.3%) |
| GED | 0 | 0 | 0 | 1 (3.3% |
| High school diploma | 3 (33.3%) | 2 (10%) | 10 (33.3%) | 8 (26.6%) |
| 2-year college degree (Associate's or Technical degree) | 2 (22.2%) | 4 (20%) | 4 (13.3%) | 5 (16.6%) |
| 4-year college degree (Bachelor's degree) | 2 (22.2%) | 4 (20%) | 12 (40%) | 9 (30%) |
| Graduate degree (Master's, Doctorate, Medical, etc.) | 1 (11.1%) | 5 (25%) | 4 (13.3%) | 6 (20%) |
| Seasonal allergies? | | | | |
| Yes | 7 (77.7%) | 10 (50%) | 17 (56.6%) | 8 (26.6%) |
| No | 2 (22.2%) | 10 (50%) | 13 (43.3%) | 22 (73.3%) |
| Still have tonsils | | | | |
| No, my tonsils have been removed | 2 (22.2%) | 3 (15%) | 3 (10%) | 5 (16.6%) |
| Yes, I still have my tonsils | 7 (77.7%) | 17 (85%) | 27 (90%) | 25 (83.3%) |
| I don't know | 0 | 0 | 0 | 0 |
| Family history of any of the following diseases | | | | |
| Crohn's Disease | 4 (44.4%) | 4 (20%) | 1 (3.3%) | 1 (3.3%) |
| Ulcerative Colitis | 2 (22.2%) | 2 (10%) | 3 (10%) | 3 (10%) |

TABLE 3-continued

Patient Demographic Data.

| Question on Demograhic Form | Symptomatic Crohn's Disease Patients (n = 9) | Asymptomatic Crohn's Disease Patients (n = 20) | Pediatric Healthy Controls (n = 30) | Adult Healthy Controls (n = 30) |
|---|---|---|---|---|
| Irritable Bowel Syndrome (IBS) | 2 (22.2%) | 2 (10%) | 3 (10%) | 3 (10%) |
| Celiac Disease | 0 | 1 (5%) | 3 (10%) | 0 |
| Other | 0 | 0 | 0 | 0 |
| Taken antibiotics in the last year | | | | |
| No | 1 (11.1%) | 6 (30%) | 25 (83.3%) | 13 (43.3%) |
| Yes | 8 (88.8%) | 13 (65%) | 5 (16.6%) | 10 (33.3%) |
| I don't know | 0 | 1 (5%) | 0 | 1 (3.3%) |
| Experienced any of the following health problems? | | | | |
| Heartburn in the last year | 3 (33.3%) | 5 (25%) | 6 (20%) | 5 (16.6%) |
| Cavities in the last year | 2 (22.2%) | 3 (15%) | 5 (16.6%) | 7 (23.3%) |
| Diarrhea in the last month | 8 (88.8%) | 4 (20%) | 1 (3.3%) | 1 (3.3%) |
| Vomiting in the last month | 3 (33.3%) | 2 (10%) | 2 (6.6%) | 1 (3.3%) |
| Estimated hours of sleep in the last night | | | | |
| Less than 4 hours | 0 | 1 (5%) | 0 | 3 (10%) |
| 4-6 hours | 3 (33.3%) | 1 (5%) | 1 (3.3%) | 6 (20%) |
| 6-7 hours | 1 (11.1%) | 5 (25%) | 8 (26.6%) | 6 (20%) |
| 7-8 hours | 2 (22.2%) | 4 (20%) | 7 (23.3%) | 10 (33.3%) |
| 8-9 hours | 0 | 3 (15%) | 7 (23.3%) | 5 (16.6%) |
| More than 9 hours | 3 (33.3%) | 6 (30%) | 7 (23.3%) | 0 |
| Smoker in the home? | | | | |
| Yes | 0 | 2 (10%) | 5 (16.6%) | 6 (20%) |
| No | 9 (100%) | 18 (90%) | 25 (83.3%) | 24 (80%) |
| Personal smoking history (for healthy controls 18 and older) | | | | |
| Never smoked | 1 (11.1%) | 1 (5%) | — | 19 (63.3%) |
| Former smoker | — | — | — | 7 (23.3%) |
| Current smoker | — | 1 (5%) | — | 4 (13.3%) |
| Weekly alcohol intake? (for healthy controls 18 and older) | | | | |
| Less than 1 drink/week | 1 (11.1%) | 2 (10%) | — | 20 (66.6%) |
| 1-7 drinks/week | — | — | — | 10 (33.3%) |
| 7+ drinks/week | — | — | — | 0 |

Sample Collection and Testing

Saliva sample collection and testing. For all subjects, saliva samples were collected at the time of enrollment. For Crohn's patients, saliva samples were also collected upon follow-up, concurrent with stool sample collection. Sample collection was performed by having patients spit into a conical tube to provide 2 mL of saliva under the supervision of the study staff. These tubes were then labeled, and transferred to the laboratory, where sample was aliquoted into storage vials and stored at −80 C until they were retrieved for analysis. One vial of saliva sample was provided for testing using enzyme linked immunoassay to quantitate the relative quantities of the carbohydrate histo-blood group antigens: H, Lewis b, Lewis y, Lewis a, Lewis x, sialyl Lewis a, and sialyl Lewis x.

Stool sample collection and testing. Stool sample collection was limited to Crohn's patients, symptomatic and asymptomatic. At the time of enrollment, patients were given a stool sample collection kit, and requested to collect their sample at home and send the sample via a courier service. The courier service transported the samples on dry ice within 2 hours from the patient's home to the lab. Samples were and immediately frozen at −80 C, until shipment. Periodically, samples were removed from storage and placed on dry ice for shipment for analysis. While stool sample collection required significant additional work to obtain samples from outpatients, an overall 79% collection rate was achieved: 8 (89%) of 9 symptomatic patients and 15 (75%) of 20 asymptomatic patients.

Results (i) Comparison of Salivary Glycans Across Patient Populations.

Figure 3:
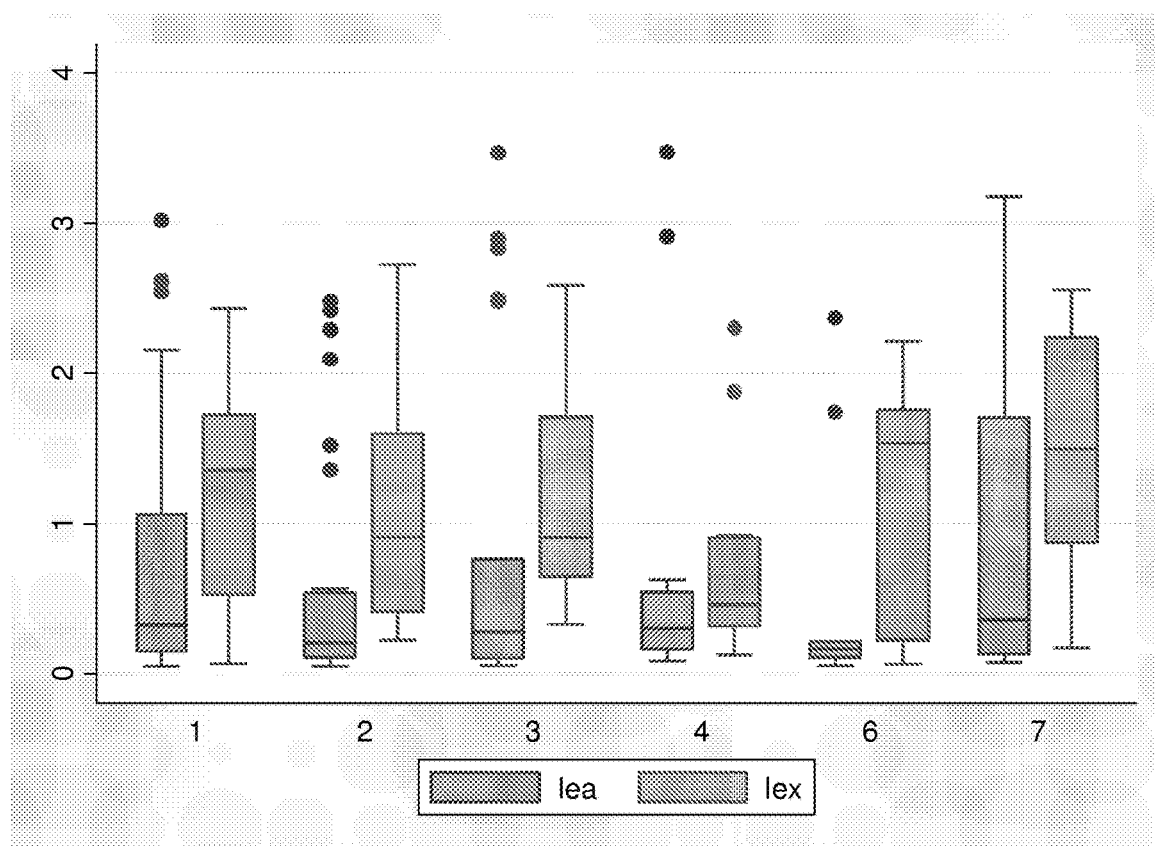
FIG. 3 is a boxplot showing optical density values for Lewis a (lea) and Lewis x (lex) salivary antigens in several patient populations. The y axis indicates the optical density (O.D.) value of the salivary antigens. For each group (1-7), the left box is lea and the right box is lex.
Figure 4:
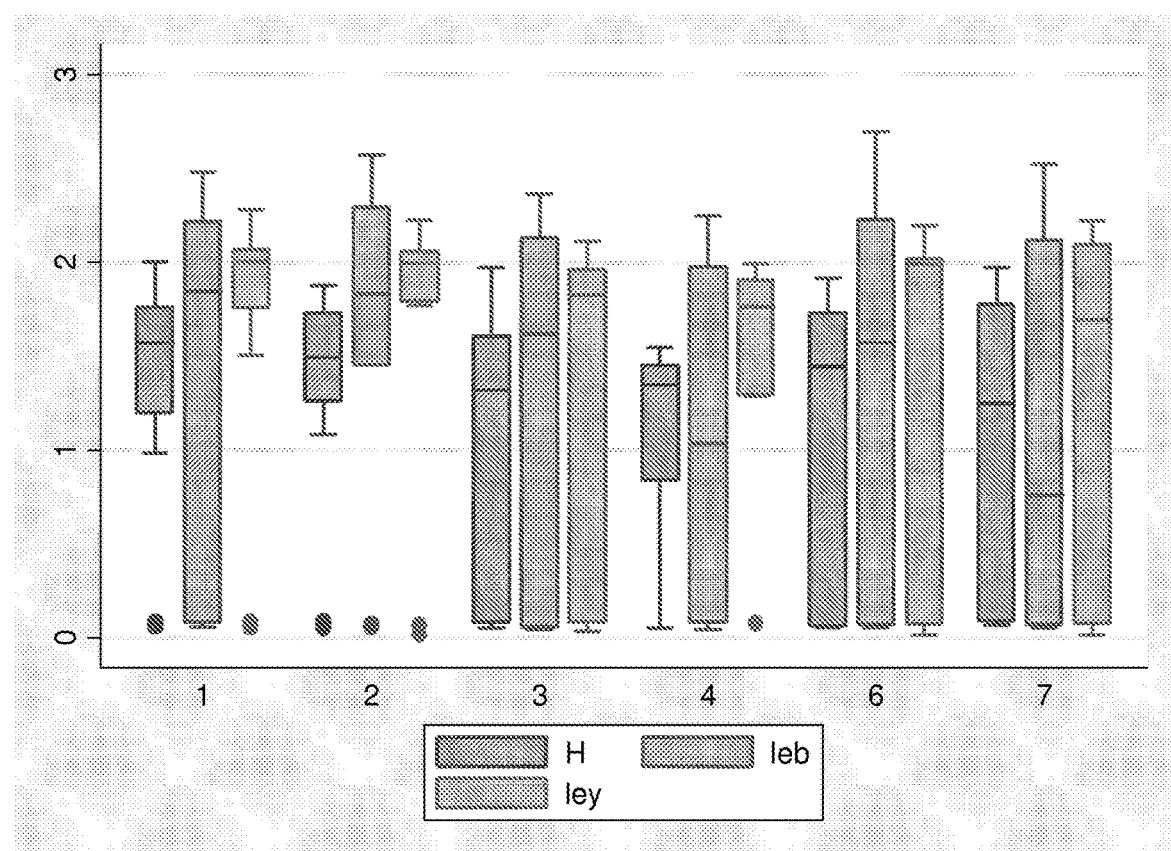
FIG. 4 is a boxplot showing optical density values for H antigen (H), Lewis b (leb) and Lewis y (ley) salivary antigens in several patient populations. The y axis indicates the O.D. value of the salivary antigens. For each group (1-7), the left box is H, the middle box is leb, and the right box is ley.
Figure 5:
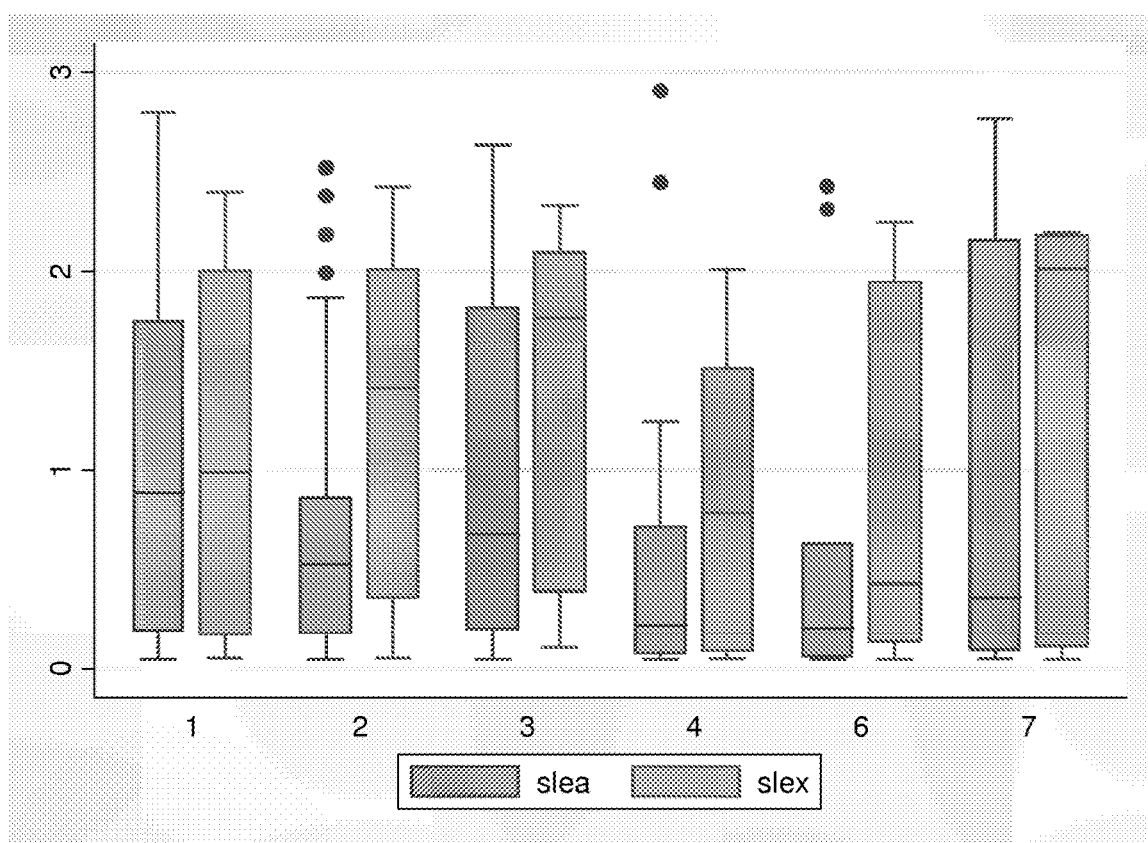
FIG. 5 is a boxplot showing optical density values for sialyl Lewis a (slea) and sialyl Lewis x (slex) salivary antigens in several patient populations. The y axis indicates the O.D. value of the salivary antigens. For each group (1-7), the left box is slea and the right box is slex.

FIGS. 3-5 provide boxplots comparing the patient groups for each salivary antigen. No significant differences were identified among patient groups overall when analyzed univariately using nonparametric tests. However, some important specific differences in salivary glycan values were discovered after detailed analysis. For example, H antigen, Lewis b and Lewis y values were significantly higher ($p<0.05$) in healthy controls than CD patients as a whole. Sialyl Lewis x and Lewis x, and the combination thereof, were found to differ in symptomatic and asymptomatic patients as described below.

(ii) Statistical Analysis of Samples Collected at the Time of Patient Enrollment for Asymptomatic and Symptomatic CD Patients.

Figure 6:
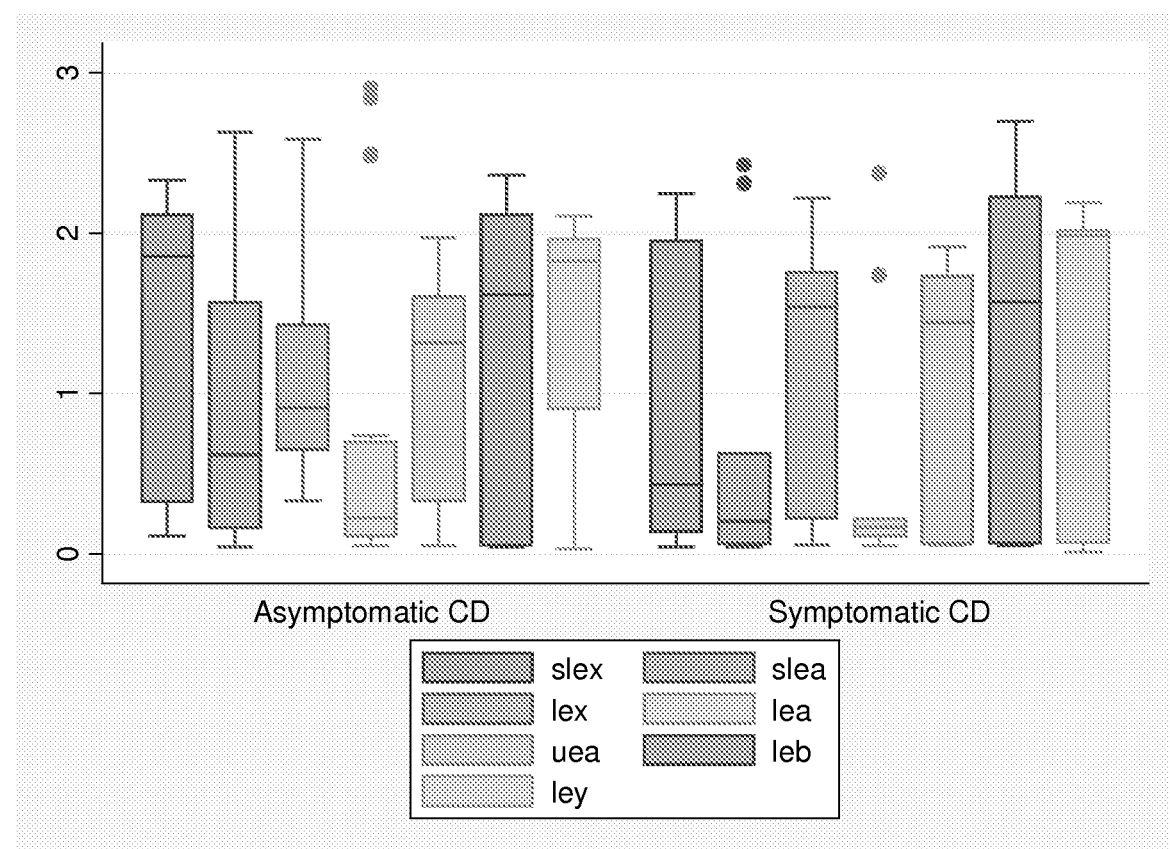
FIG. 6 is a boxplot showing salivary antigens tested in samples collected at the time of enrollment from Asymptomatic Crohn's Disease (CD) patients (n=20) compared to Symptomatic CD patients (n=9). slex=Sialyl Lewis x, slea=sialyl Lewis a, lex=Lewis x, lea=Lewis a, uea=H antigen (identified by Ulex europaeus antigen), leb=Lewis b, and ley=Lewis y. The y axis indicates the O.D. value of the salivary antigens. For each group (asymptomatic or symptomatic CD), the boxes from left to right are slex, slea, lex, lea, uea, leb, and ley.

For this analysis, only the 9 symptomatic patients, and 20 asymptomatic patients were included. By the non-parametric Kruskal-Wallis test there were no significances identified in the salivary glycan values comparing these patient groups. FIG. 6 shows the optical density values of the glycans (histo-blood group antigens) tested.

(iii) Statistical Analysis of Saliva Samples Collected after the Enrollment Visit, at Home, by Crohn's Patients Concurrent with Stool Sample Collection.

Figure 7:
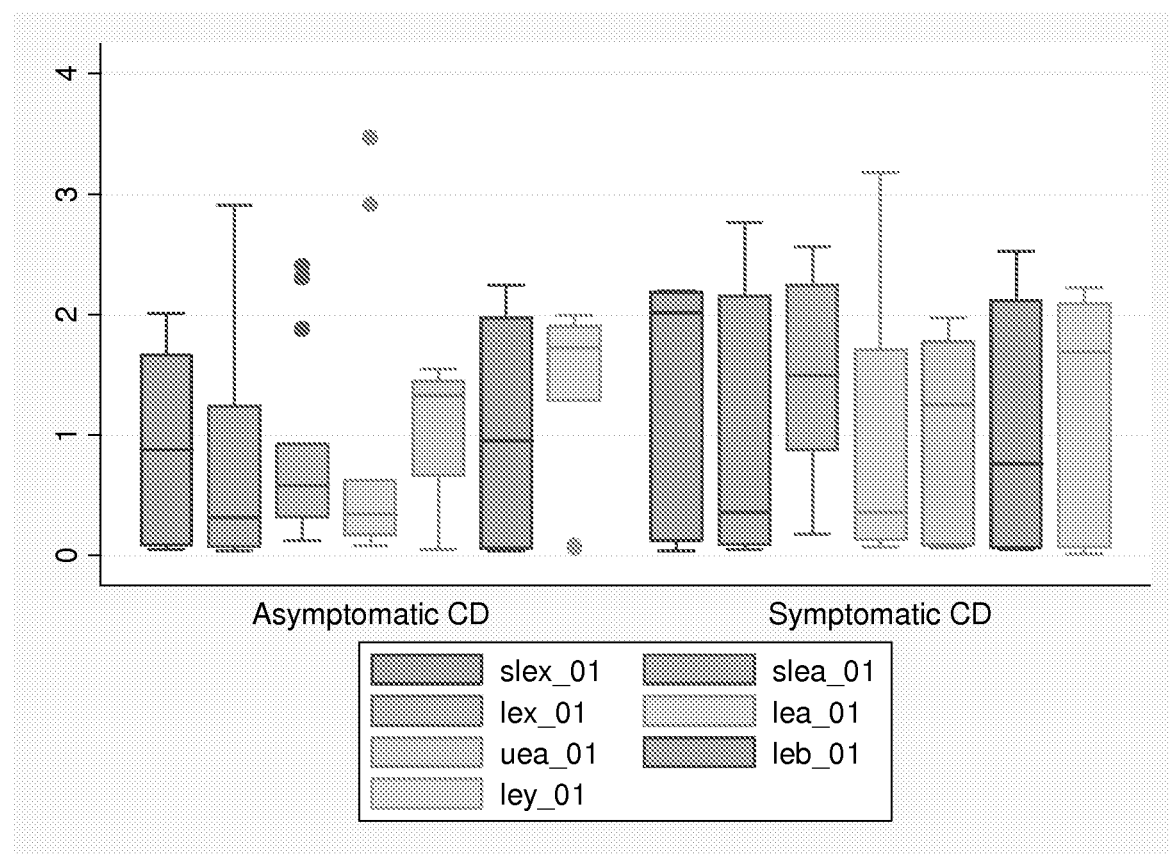
FIG. 7 is a boxplot showing salivary antigens tested in the follow-up sample collected by the patient at home, following the clinical/enrollment visit. The patient groups were Asymptomatic Crohn's Disease (CD) patients (n=15) compared to Symptomatic CD patients (n=8). The y axis indicates the O.D. value of the salivary antigens. For each group (asymptomatic or symptomatic CD), the boxes from left to right are slex, slea, lex, lea, uea, leb, and ley. The _01 indicates that it is a follow-up sample.
Figure 8:
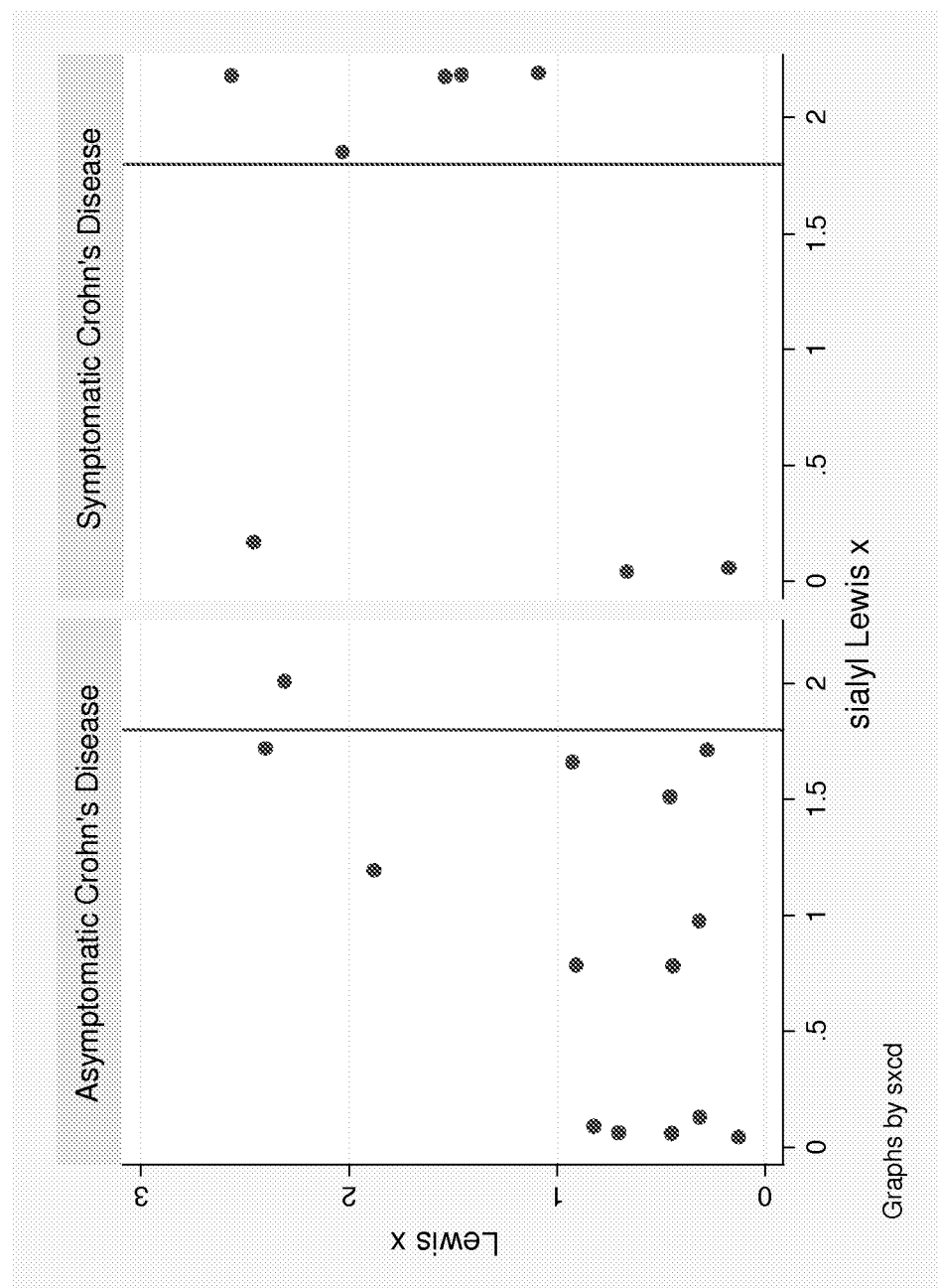
FIG. 8 is two graphs showing Lexis x and sialyl Lewis X values in asymptomatic and symptomatic CD patients measured by ELISA. The values for the x and y-axes are optical density (O.D.) values. The line through each graph marks the 1.8 O.D. value, which may serve as a cut-point for a high sLe x value.

For this analysis, 8 symptomatic Crohn's patients and 14 asymptomatic Crohn's patients were assessed. There was a significant difference between these patients in relation to sialyl Lewis x (sLe x) and Lewis x (Le x). The best prediction was obtained by the combination of these two antigens. FIG. 7 shows the optical density values of all of the glycans (histo-blood group antigens) tested. FIG. 8 shows the optical density values of Lewis x and sialyl Lewis x.

The optical density cutpoints, including the predictive value, sensitivity and specificity, are summarized below for sialyl Lewis x, Lewis x, or the combination of both markers.
1. Single Marker: sLex>1.8
    Symptomatic Crohn's 5/8 (62.8%)
    Asymptomatic Crohn's 1/14 (7.1%)
    Odds ratio=21. 7 (95% CI 1.4, 1100), exact p=0.011
    Predictive value=77.7%, sensitivity=62.5%, specificity=92.9%
2. Alternate Single Marker: Lewis x>1.0
    Symptomatic Crohn's 6/8 (75.0%)
    Asymptomatic Crohn's 3/14 (21.4%)
    Odds ratio=11.0 (95% CI 1.05, 148), exact p=0.026
    Predictive value=76.8%, sensitivity=75.0%, specificity=78.6%
3. Combination of sLex>1.8 and high Lewis x>1.0 if sLex is very low (<0.5)
    Symptomatic Crohn's 6/8 (75.0%)
    Asymptomatic Crohn's 1/14 (7.1%)
    Odds ratio=39 (95% CI 2.2, 1924), exact p=0.002
    Predictive value=83.9%, sensitivity=75.0%, specificity=92.9%

Figure 9:
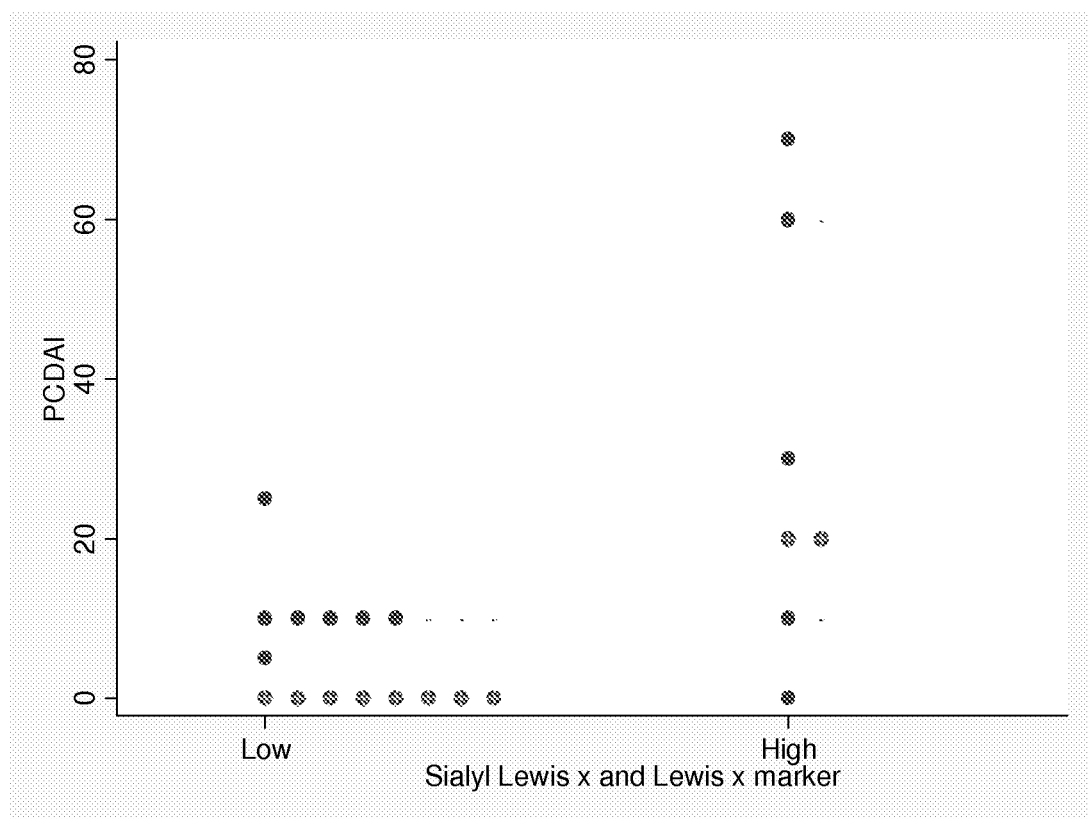
FIG. 9 is a dotplot of the values for each subject on the short PCDAI scale (y-axis) in relation to the combination of sLex and Lewis x (high vs low).

The combination of sLex and Lewis x was significantly associated with the short Pediatric Crohn's Disease Activity Index (PCDAI) scale (Kruskal-Wallis test, p=0.008, FIG. 9). The short PCDAI scale is used clinically to determine Crohn's Disease symptom severity.

(iv) Comparison of First and Second Samples: Change Over Time.

Of the 9 symptomatic Crohn's patients, a second sample at a later time point was received from 8 subjects. Among these 8 subjects, three remained essentially the same over time and five changed dramatically. There was no correlation between these two samples. The sialyl Lewis X values for the first and second samples are shown below in Table 4.

TABLE 4

Sample S Lex values for symptomatic Crohn's patients.

| Patient ID | 1st sample value | 2nd sample value | Comments |
| --- | --- | --- | --- |
| 402 | 1.949 | 2.18 | The first & second samples of the subject remained consistent. |
| 406 | 2.248 | 1.852 | The first & second samples of the subject remained consistent. |
| 409 | .053 | .045 | The first & second samples of the subject remained consistent. |
| 401 | .432 | 2.195 | The first & second samples of the subject remained consistent. |
| 403 | .35 | 2.186 | The subject started with low values but at followup had high values. |

TABLE 4-continued

Sample S Lex values for symptomatic Crohn's patients.

| Patient ID | 1st sample value | 2nd sample value | Comments |
| --- | --- | --- | --- |
| 405 | .136 | 2.178 | The subject started with low values but at followup had high values. The subject started with low values but at followup had high values. |
| 404 | 2.156 | .172 | The subject started with high values but at followup had low values. |
| 407 | 1.728 | .062 | The subject started with high values but at followup had low values. |

Of the 20 asymptomatic patients, a second sample at a later time point was received from 15 subjects. The values of first and second samples were highly correlated and are summarized in Table 5, Spearman's rho=0.64, p=0.011. Samples of symptomatic and asymptomatic subjects indicate variation within individuals over time, which may be highly relevant to using sLex for monitoring health status.

TABLE 5

Sample S Lex values for asymptomatic Crohn's patients.

| Patient ID | 1st sample value | 2nd sample value | Comments |
| --- | --- | --- | --- |
| 304 | 2.136 | 2.009 | This patient had similar sLex values for initial and follow-up samples. |
| 330 | 2.088 | 1.724 | This patient had similar sLex values for initial and follow-up samples. |
| 307 | 1.805 | 1.661 | This patient had similar sLex values for initial and follow-up samples. |
| 317 | 1.683 | 1.716 | This patient had similar sLex values for initial and follow-up samples. |
| 320 | 2.332 | 1.511 | This patient had similar sLex values for initial and follow-up samples. |
| 308 | .159 | .062 | This patient had similar sLex values for initial and follow-up samples. |
| 309 | .392 | .782 | This patient had similar sLex values for initial and follow-up samples. |
| 313 | .154 | .048 | This patient had similar sLex values for initial and follow-up samples. |
| 315 | .257 | .09 | This patient had similar sLex values for initial and follow-up samples. |
| 301 | 2.097 | 1.197 | This patient had high initial sample values but intermediate follow-up sample values. |
| 310 | 2.169 | .975 | This patient had high initial sample values but intermediate follow-up sample values. |
| 340 | 2.078 | 1.375 | This patient had high initial sample values but intermediate follow-up sample values. |
| 312 | 1.238 | .13 | This patient had an intermediate initial value, with low follow-up value. |
| 303 | 2.026 | .061 | This patient had a high initial value, with low follow-up value. |
| 314 | 1.91 | .785 | This patient had a high initial value, with low follow-up value. |

(v) Factors Associated with Sialyl Lewis x and Lewis x.

Figure 10:
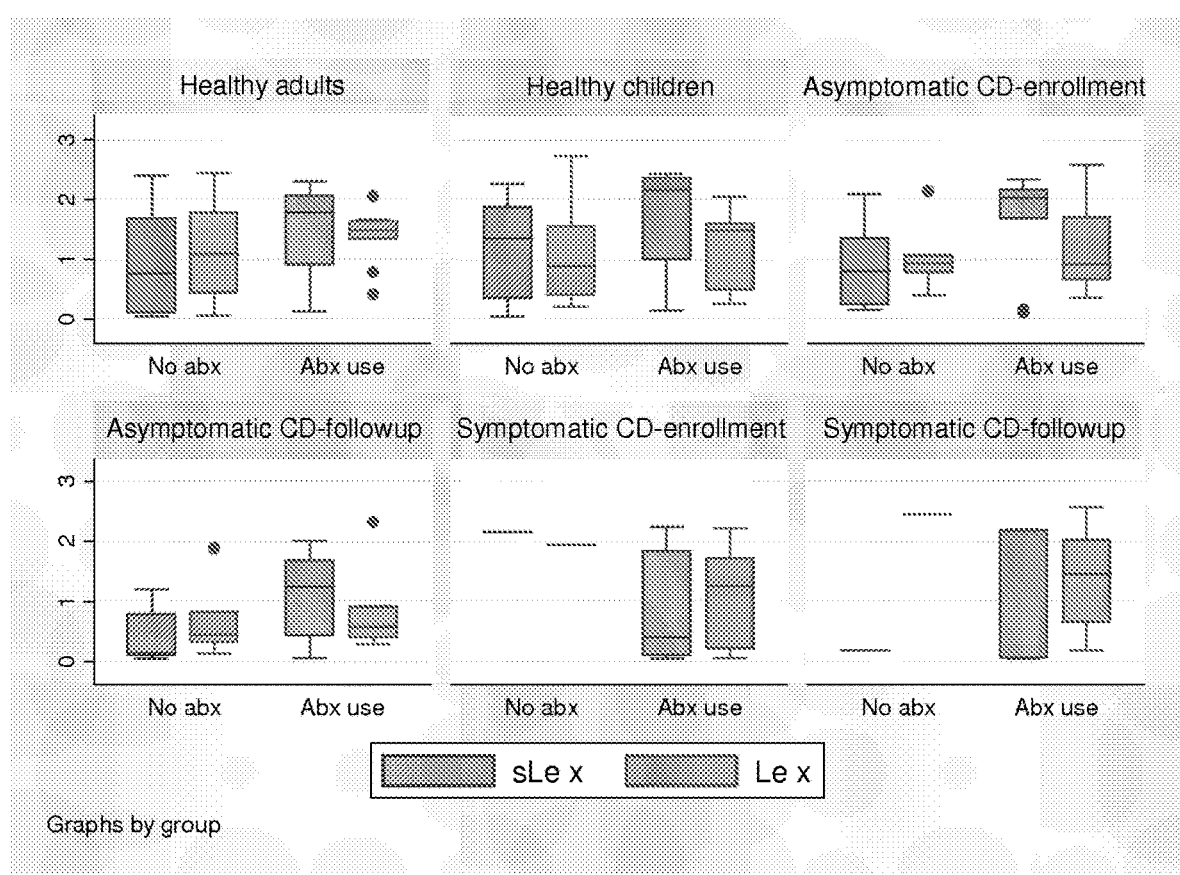
FIG. 10 is a boxplot of sialyl Lewis x (sLex) and Lewis x (Lex) O.D. values by history of antibiotic use. The y axis indicates the O.D. value. abx use=history of antibiotic use, no abx=no history of antibiotic use. For each group in each plot, the left box is sLex and the right box is Lex.
Figure 11:
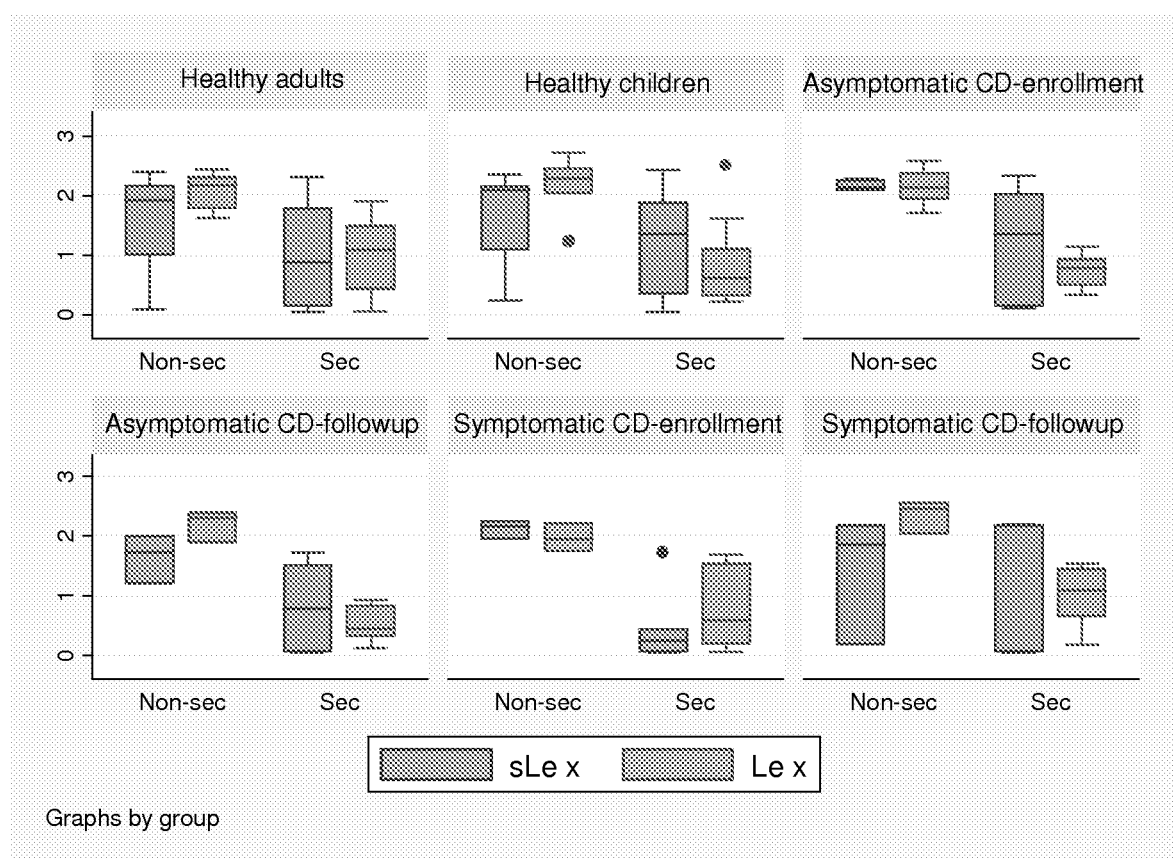
FIG. 11 is a boxplot of sialyl Lewis x (sLex) and Lewis x (Lex) O.D. values by secretor status. The y axis indicates the O.D. value. Non-sec=non-secretor, sec=secretor. For each group in each plot, the left box is sLex and the right box is Lex.
Figure 12A:
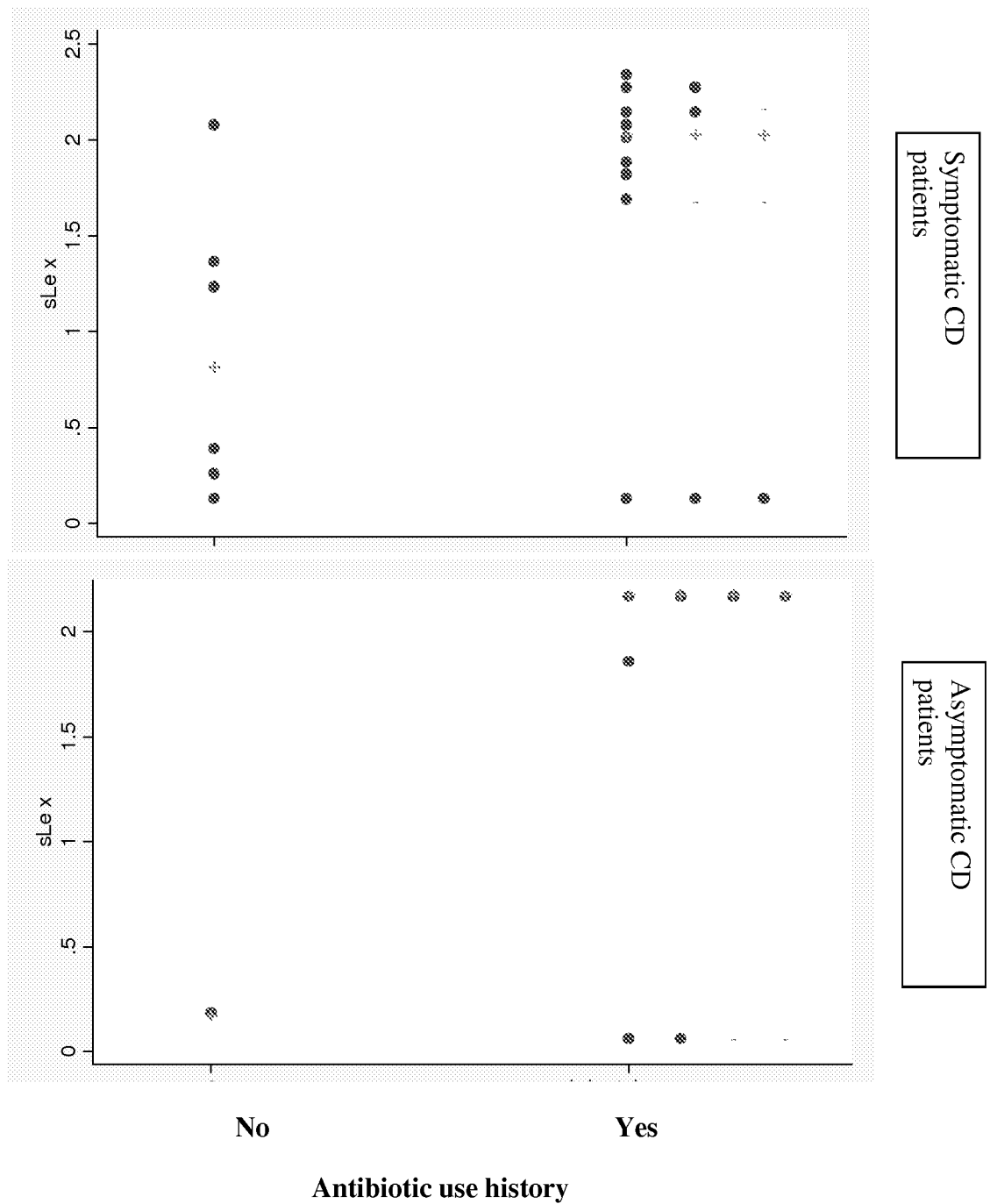
FIG. 12A shows two graphs of sialyl Lewis x (sLex) O.D. values from samples collected at the enrollment visit for symptomatic and asymptomatic CD patients who either did or did not have a history of antibiotic use.
Figure 12B:
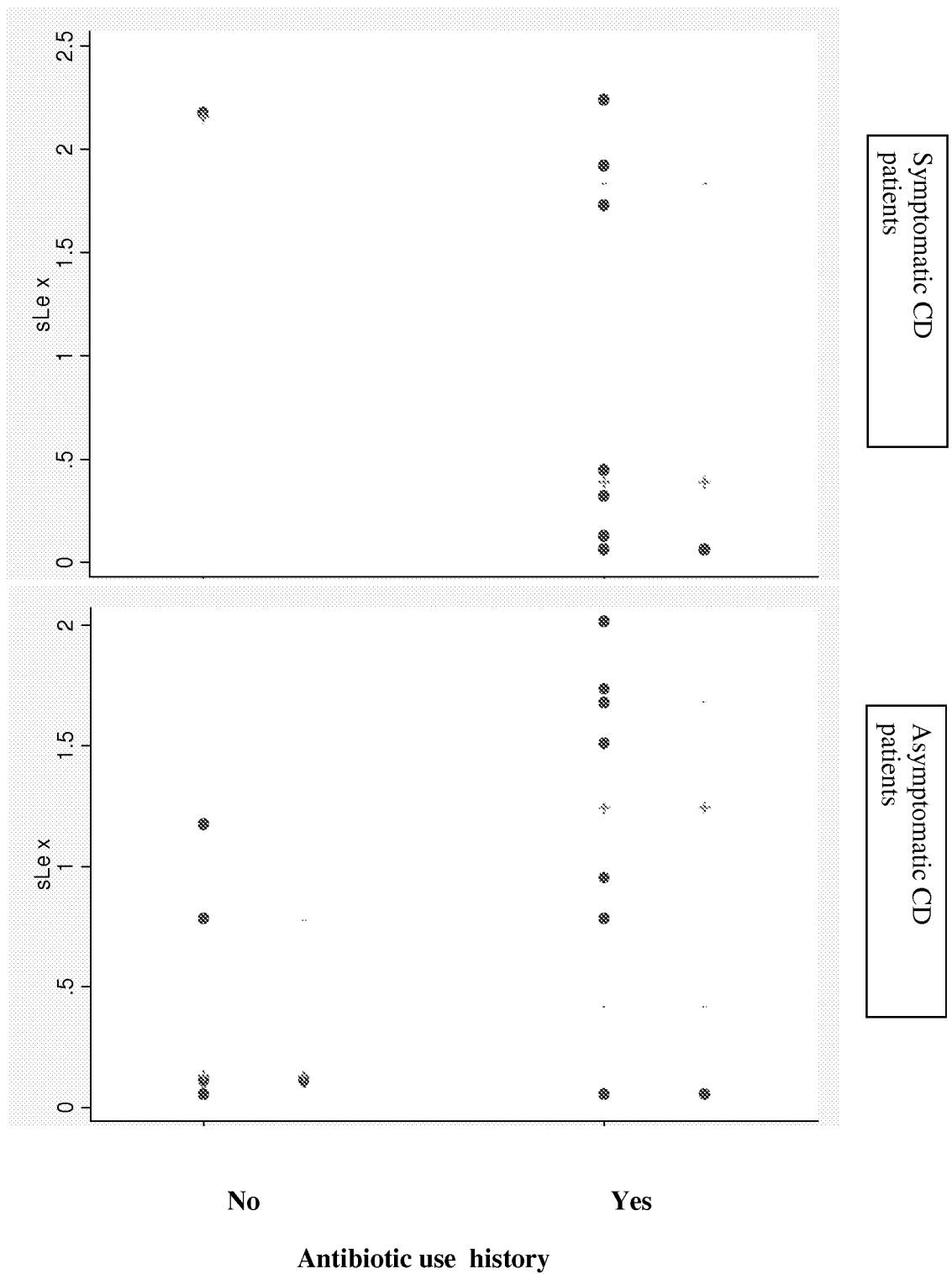
FIG. 12B shows two graphs of sialyl Lewis x (sLex) O.D. values from samples collected at the followup visit for symptomatic and asymptomatic CD patients who either did or did not have a history of antibiotic use.

Two factors were associated with salivary sialyl Lewis x—history of antibiotic use in the past year (p=0.002), and secretor status (p<0.001), in an ANOVA model that included study group (which was not significant). No other factors were associated with sLex. Secretor status was significantly associated with levels of Lewis x, but not history of antibiotic use. FIG. 10 shows plots of sialyl Lewis X and Lewis X optical density values by history of antibiotic use. FIG. 11 shows plots of sialyl Lewis X and Lewis X optical density values by secretor status. FIG. 12 shows plots of sialyl Lewis X optical density values in symptomatic and asymptomatic CD patients at two collection time points by history of antibiotic use.

(vi) Comparison with Fecal Markers Measured.

Figure 13:
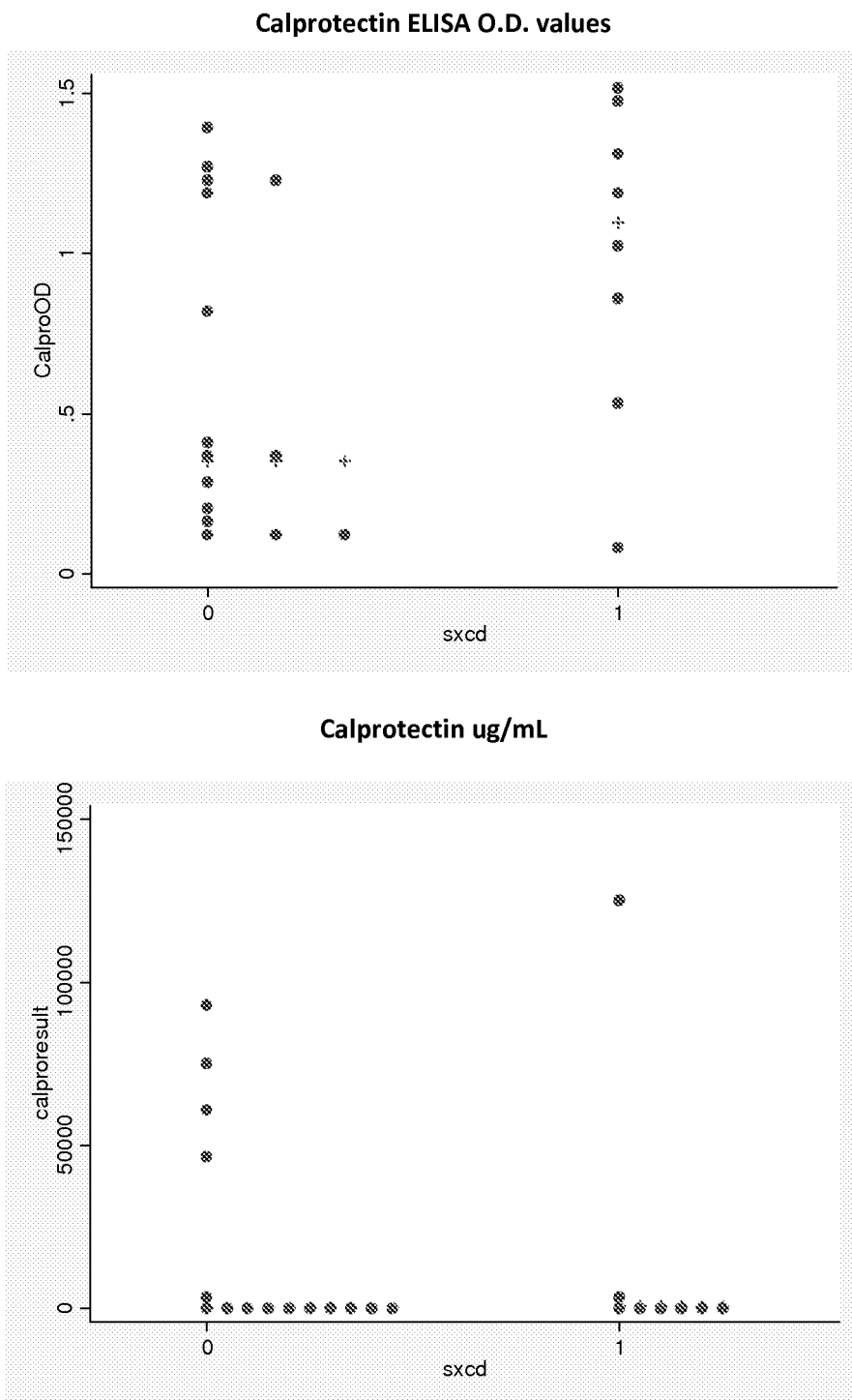
FIG. 13 shows two graphs of fecal calprotectin values in relation to patient symptom group. The upper graph shows ELISA O.D. values for calprotectin. The lower graph shows the amount of calprotectin (ug/mL). P=0.074, comparing Calprotectin O.D. value<0.5 between sx and asx Crohn's. 1=symptomatic CD, 0=asymptomatic CD at followup.
Figure 14:
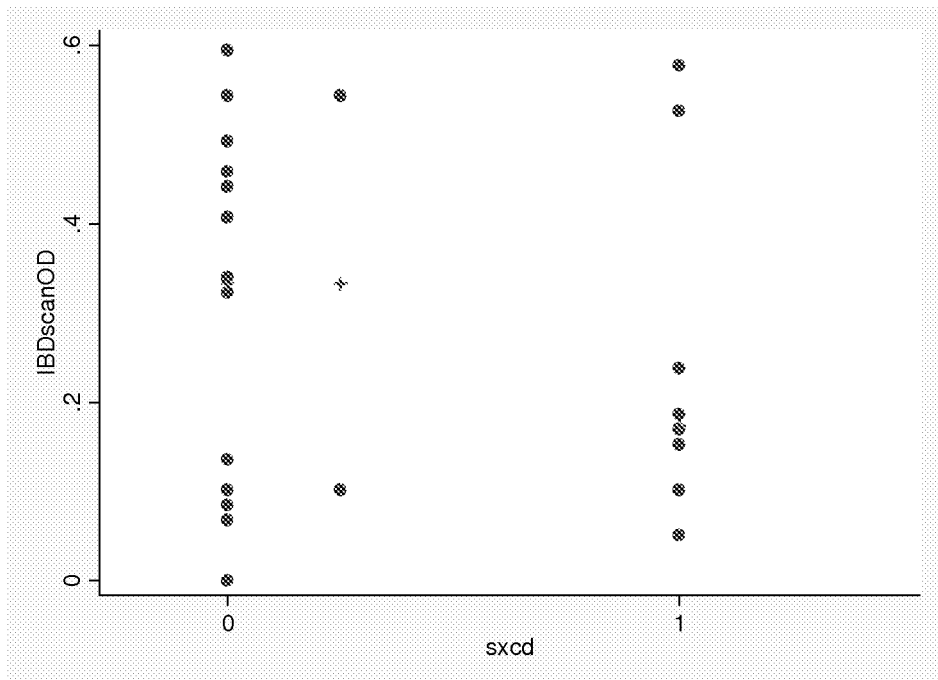
FIG. 14 shows two graphs of the IBD-SCAN® values in relation to patient symptom group. The upper graph shows O.D. value. The lower graph shows the amount (ug/mL). 1=symptomatic CD, 0=asymptomatic CD at followup.
Figure 14:
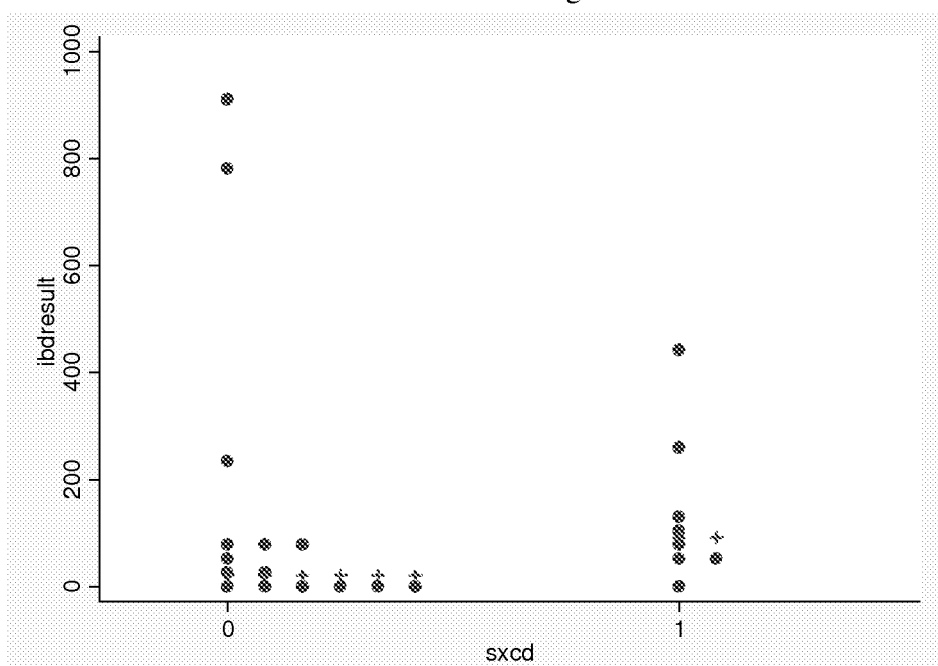
Figure 15:
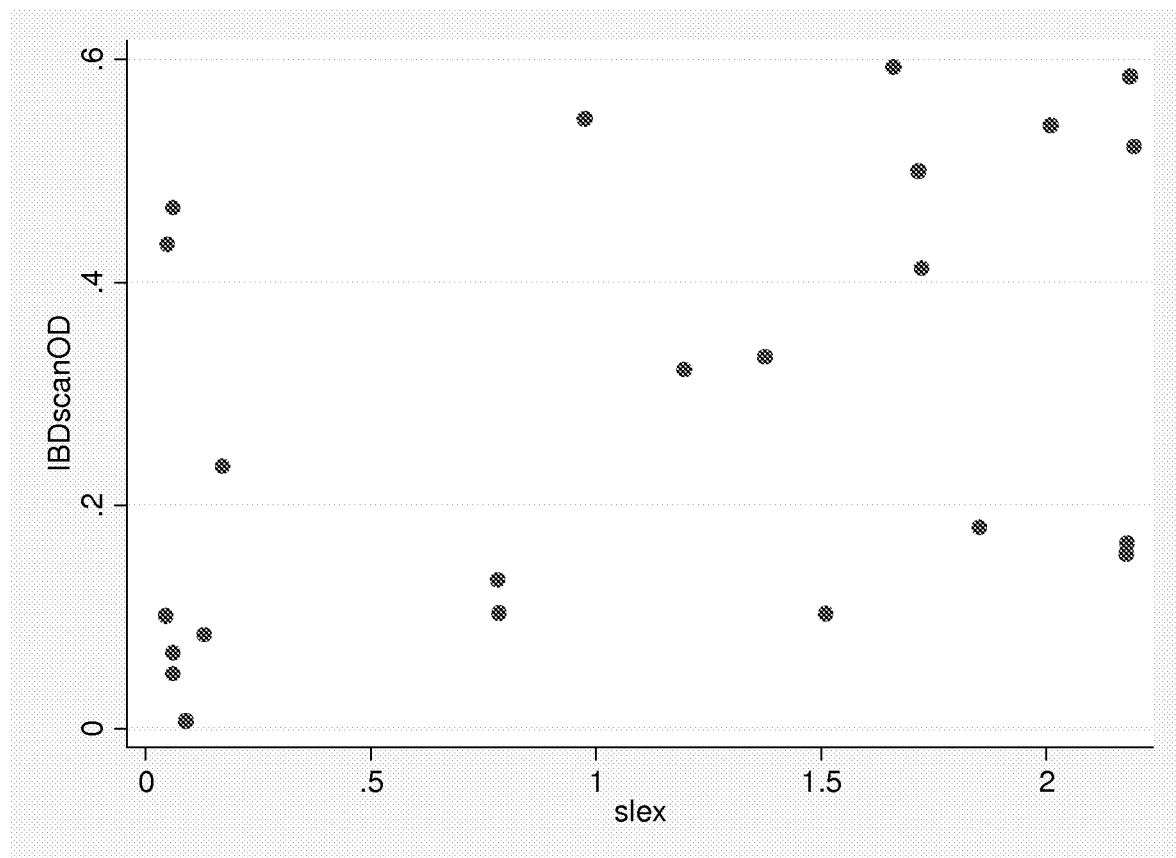
FIG. 15 shows a scatterplot of the IBD-SCAN® and salivary sialyl Lewis x (sLe x) O.D. values.

Fecal Calprotectin values were measured and assessed in relation to patient symptom group (FIG. 13). IBD-SCAN® optical density values were also measured and assessed in relation to patient symptom group (FIG. 14). The IBD-SCAN® test is a commercially available quantitative ELISA for measuring concentrations of fecal lactoferrin, a marker of fecal leukocytes. An elevated level is an indicator of intestinal inflammation. The IBD-SCAN® values were compared to the sialyl lewis X optical density values. It was found that the sialyl Lewis x optical density values were significantly correlated with the IBD-SCAN® optical density value, Spearman's rho=0.49, p=0.016 (FIG. 15).

CONCLUSIONS

Sialyl Lewis x, alone or in combination with Lewis x, appears promising to examine in larger, longitudinal studies of patient self-monitoring, based on the samples collected by patients after their initial enrollment visit. Single antigen predictive value was 77% based on the identified cut-points. Use of combinations of antigen values increased the predictive value to 84%. Salivary sialyl Lewis x was associated with history of antibiotic use in the past year, whether in control patients or in Crohn's patients. Sialyl Lewis x was associated with patient symptom scores, and was correlated with the IBD-SCAN® O.D. values. In summary, this pilot study provides intriguing evidence of the potential role of salivary glycans, particularly sialyl Lewis x, as a biomarker for patient self-monitoring of health status and symptom flares.

REFERENCES

Chaturvedi P, Warren C D, Altaye M, et al. (2001) Fucosylated human milk oligosaccharides vary between individuals and over the course of lactation. Glycobiology; 11: 365-372.
Henry, S. M. (2001). Molecular diversity in the biosynthesis of GI tract glycoconjugates. A blood-group-related chart of microorganism receptors. Transfus Clin Biol 8(3): 226-230.
Huang P, Farkas T, Marionneau S, Zhong W, Ruvoen-Clouet N, Morrow A L, Altaye M, Pickering L K, Newburg D S, LePendu J, Jiang X. (2003) Noroviruses Bind to Human ABO, Lewis, and Secretor Histo-Blood Group Antigens: Identification of 4 Distinct Strain-Specific Patterns. J Infect Dis. 188; 19-31.
Loftus, E. V., Jr. (2004). Clinical epidemiology of inflammatory bowel disease: Incidence, prevalence, and environmental influences. Gastroenterology 126(6): 1504-1517.
McGovern D P B et al. (2010) Fucosyltransferase 2 (FUT2) non-secretor status is associated with risk of Crohn's Disease. Human Molecular Genetics.
Morrow A L, et al. (2011) Fucosyltransferase 2 (FUT2) non-secretor and low secretor status predicts severe outcomes in premature infants. J Pediatr. May; 158(5):745-51.
Nakayama, F., S. Nishihara, et al. (2001). CD15 expression in mature granulocytes is determined by alpha 1,3-fucosyltransferase IX, but in promyelocytes and monocytes by alpha 1,3-fucosyltransferase IV. The Journal of biological chemistry 276(19): 16100-16106.
Niverge D, Grimmonprez L, Cassanas G, Bardet L, Solere M. (1990) Discriminant carbohydrate components of human milk according to donor secretor types. J Pediatr Gastroenterol Nutr; 11: 365-370.
Park, K. T. and D. Bass (2011). Inflammatory bowel disease-attributable costs and cost-effective strategies in the United States: a review. Inflammatory bowel diseases 17(7): 1603-1609.
Rausch P, et al. (2011) Colonic mucosa-associated microbiota is influenced by an interaction of Crohn's disease and FUT2 (Secretor) genotype. PNAS.
Thurl S, Henlcer J, Siegel M, Tovar K, Sawatzki G. (1997) Detection of four human milk groups with respect to Lewis blood group dependent oligosaccharides. Glycoconj J; 14: 795-799.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for diagnosing and treating inflammatory bowel disease, the method comprising:
    measuring a level of one or more human blood group antigens in a tissue sample of a human subject suspected of having an inflammatory bowel disease (IBD), wherein the IBD is Intestinal Colitis, Ulcerative Colitis, or Crohn's disease,
    determining a profile of the one or more human blood group antigens in the tissue sample,
    identifying the human subject as having or at risk for IBD based on the profile of the one or more human blood group antigens, and
    treating the human subject with an anti-inflammatory agent, an immune suppressant agent, an antibiotic agent, or a combination thereof;
    wherein the one or more human blood group antigens comprise one or more of sialyl Lewis x (sLe$^x$), Lewis x (Le$^x$), and Lewis b (Le$^b$).

2. The method of claim 1, wherein the one or more human blood group antigens comprise sLe$^x$, and wherein the expression profile representing an elevated level of the one or more human group blood group antigens indicates that the human subject has or is at risk for the IBD.

3. The method of claim 2, wherein the one or more human blood group antigens further comprise Le$^b$.

4. The method of claim 1, wherein the at least one or more human blood group antigens further comprise an H antigen, and wherein the expression profile representing a reduced level of the H antigen indicates that the human subject has or is at risk for IBD.

5. The method of claim 1, wherein the tissue sample is an intestinal sample, a colon biopsy sample, a biofluid sample, a saliva sample, or a stool sample.

6. The method of claim 1, wherein the level of the one or more human blood antigens is measured by an immune assay, agglutination inhibition assay, or flow cytometry.

7. The method of claim 1, wherein the one or more human blood group antigens comprises $sLe^x$ and $Le^x$.

8. The method of claim 1, wherein the one or more human blood group antigens further comprise sialyl Lewis a ($sLe^a$).

* * * * *